United States Patent [19]
Pomeranz et al.

[11] Patent Number: 5,895,417
[45] Date of Patent: Apr. 20, 1999

[54] DEFLECTABLE LOOP DESIGN FOR A LINEAR LESION ABLATION APPARATUS

[75] Inventors: Mark L. Pomeranz, Los Gatos; Troy J. Chapman, Sunnyvale; Darren R. Sherman, Los Altos, all of Calif.; Scott Tedder, Chandler, Tex.; Steven C. Anderson, Sunnyvale, Calif.

[73] Assignee: Cardiac Pathways Corporation, Sunnyvale, Calif.

[21] Appl. No.: 08/965,353

[22] Filed: Nov. 6, 1997

Related U.S. Application Data

[63] Continuation-in-part of application No. 08/611,656, Mar. 6, 1996, Pat. No. 5,800,482.

[51] Int. Cl.⁶ .................................................. A61B 17/39
[52] U.S. Cl. ..................... 607/101; 607/105; 607/99; 607/122; 607/113; 606/41
[58] Field of Search .................................. 607/96, 98, 99, 607/105, 113, 116, 122, 124, 149, 153, 101, 102; 606/27–31, 41, 42; 600/372–374, 381

[56] References Cited

U.S. PATENT DOCUMENTS

| | | | |
|---|---|---|---|
| 3,044,836 | 7/1962 | Conlon | 308/9 |
| 4,850,351 | 7/1989 | Herman et al. | 128/303 |
| 4,945,912 | 8/1990 | Langberg . | |
| 4,979,948 | 12/1990 | Geddes et al. | 606/33 |
| 5,170,803 | 12/1992 | Hewson et al. | 607/124 |
| 5,191,883 | 3/1993 | Lennox et al. | 128/401 |
| 5,230,349 | 7/1993 | Langberg . | |
| 5,234,004 | 8/1993 | Hascoet et al. . | |
| 5,236,413 | 8/1993 | Feiring | 604/21 |
| 5,281,213 | 1/1994 | Milder et al. . | |
| 5,334,193 | 8/1994 | Nardella . | |
| 5,342,357 | 8/1994 | Nardella . | |
| 5,348,554 | 9/1994 | Inman et al. . | |
| 5,368,597 | 11/1994 | Pagedas | 606/114 |
| 5,383,876 | 1/1995 | Nardella . | |

(List continued on next page.)

FOREIGN PATENT DOCUMENTS

| | | | |
|---|---|---|---|
| 0 449 491 A2 | 8/1992 | European Pat. Off. | A61N 1/05 |
| 0 539 125 A1 | 4/1993 | European Pat. Off. | A61B 17/00 |
| 1466248 | 12/1966 | France . | |
| 30 38 885 A1 | 5/1982 | Germany | A61N 1/04 |
| 1690786 A1 | 11/1991 | U.S.S.R. | A61N 1/05 |
| WO 90/07909 | 7/1990 | WIPO | A61B 17/32 |
| WO 94/08519 | 4/1994 | WIPO | A61B 17/32 |
| WO 95/15115 | 6/1995 | WIPO | A61B 5/04 |
| WO 95/34346 | 12/1995 | WIPO | A61N 1/40 |
| WO 96/00041 | 1/1996 | WIPO | A61B 17/39 |
| WO 96/00042 | 1/1996 | WIPO | A61B 17/39 |

OTHER PUBLICATIONS

Borggrefe, et al., "High Frequency Alternating Current Ablation of an Accessory Pathway in Humans," *JACC* 10 (3), pp. 576–582 (1987).

*Primary Examiner*—William E. Kamm
*Assistant Examiner*—Kennedy J. Schaetzle
*Attorney, Agent, or Firm*—Limbach & Limbach L.L.P.

[57] ABSTRACT

An apparatus for ablating body tissue, and particularly for creating linear lesions within a chamber of a patient's heart, is provided. The apparatus includes an elongate member having an ablation section which includes an infusion tube and a plurality of spaced electrodes. The infusion tube and electrodes are covered by a fluid permeable foam material, and the foam material is covered by a fluid impermeable covering having a plurality of holes formed in it. During use, the ablation section is placed against tissue to be ablated. This positioning step is facilitated because the ablation section of the inventive devices may be manipulated in various ways. When the ablation section is properly positioned, radio frequency energy is delivered to the electrodes while saline or other conductive fluid is delivered to the infusion tube. The fluid exits the infusion tube at the ablation section, contacts the electrodes, and carries RF energy from the electrodes through the foam, through the holes in the covering and into contact with the body tissue to form a burn in the body tissue.

23 Claims, 25 Drawing Sheets

U.S. PATENT DOCUMENTS

| | | | |
|---|---|---|---|
| 5,423,811 | 6/1995 | Imran et al. | |
| 5,431,696 | 7/1995 | Atlee, III | 607/124 |
| 5,443,470 | 8/1995 | Stern et al. | 607/98 |
| 5,454,370 | 10/1995 | Avitall | 128/642 |
| 5,487,385 | 1/1996 | Avitall | 128/642 |
| 5,505,730 | 4/1996 | Edwards | |
| 5,531,776 | 7/1996 | Ward et al. | 607/105 |
| 5,569,241 | 10/1996 | Edwards | 607/101 |
| 5,584,872 | 12/1996 | Lafontaine et al. | 607/116 |
| 5,626,136 | 5/1997 | Webster, Jr. | 128/642 |
| 5,643,197 | 7/1997 | Brucker et al. | 604/20 |
| 5,676,693 | 10/1997 | Lafontaine | 607/116 |
| 5,687,723 | 11/1997 | Avitall | 128/642 |
| 5,702,438 | 12/1997 | Avitall | 607/122 |
| 5,769,880 | 6/1998 | Truckai et al. | 607/101 |
| 5,797,903 | 8/1998 | Swanson et al. | 607/105 |

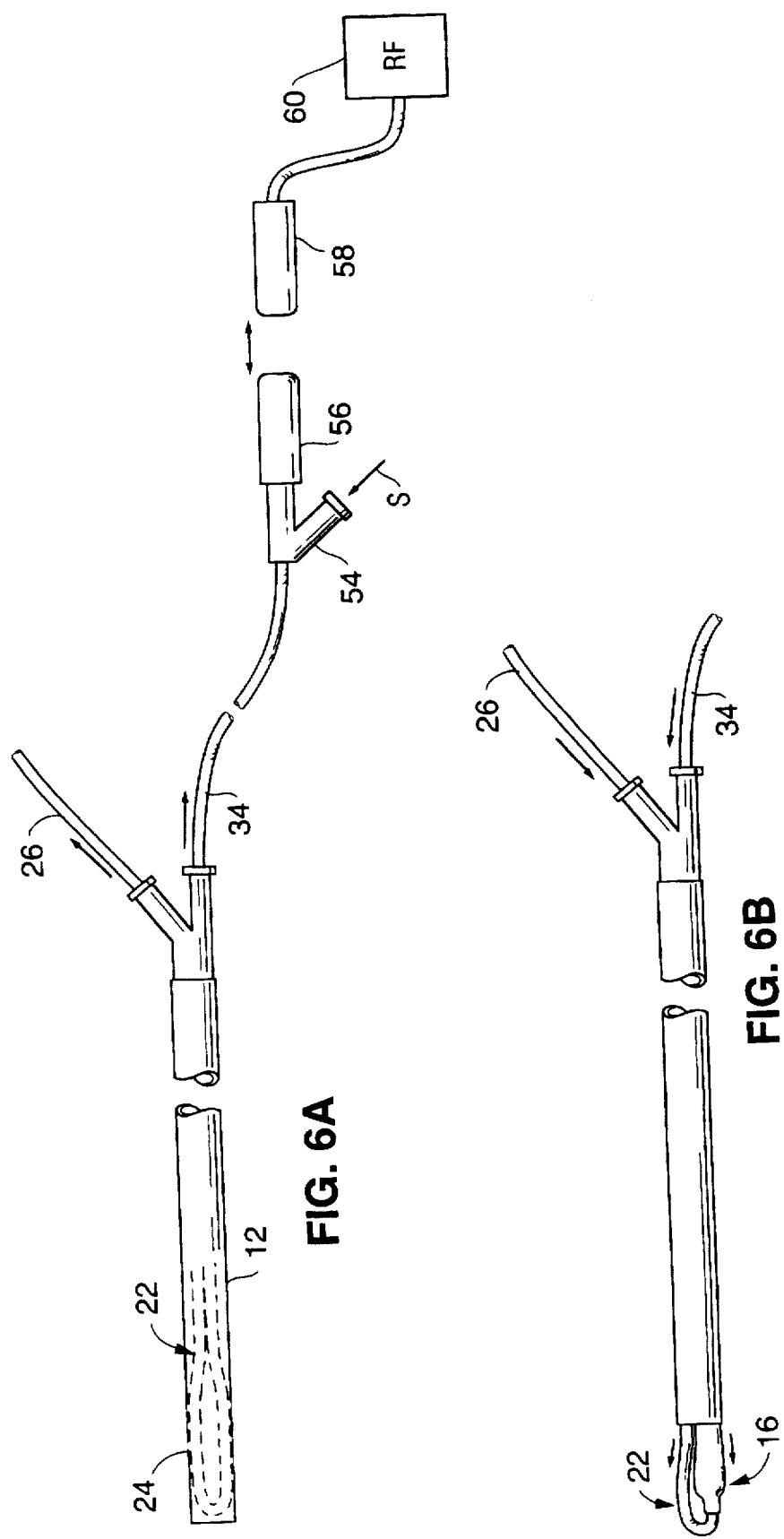

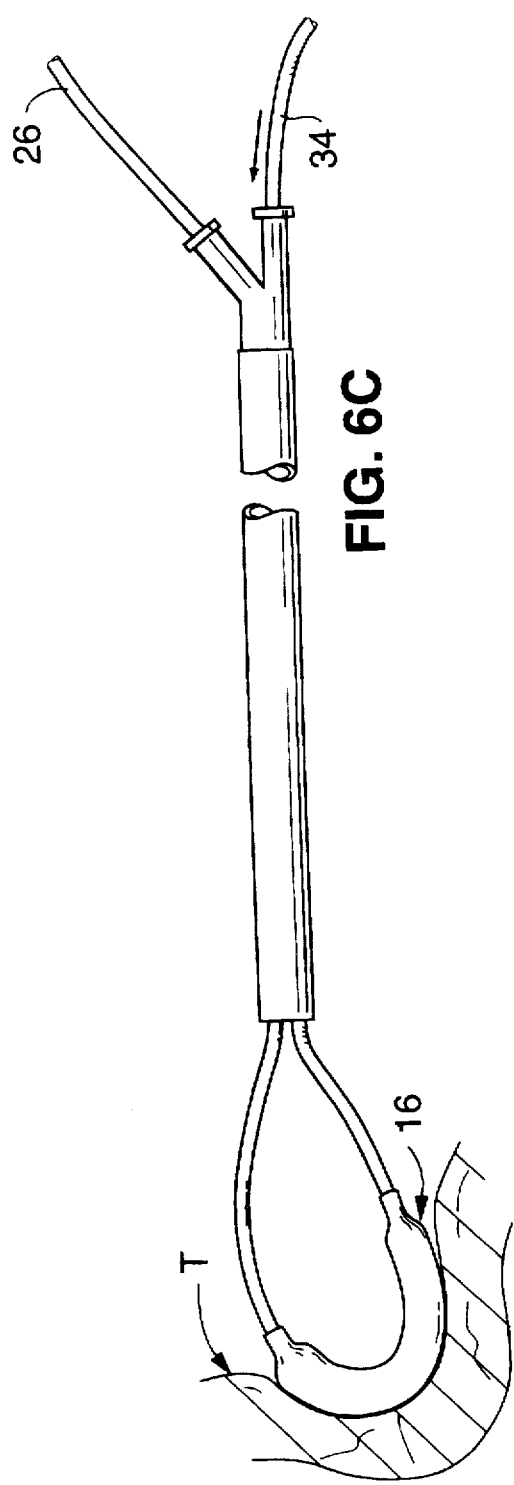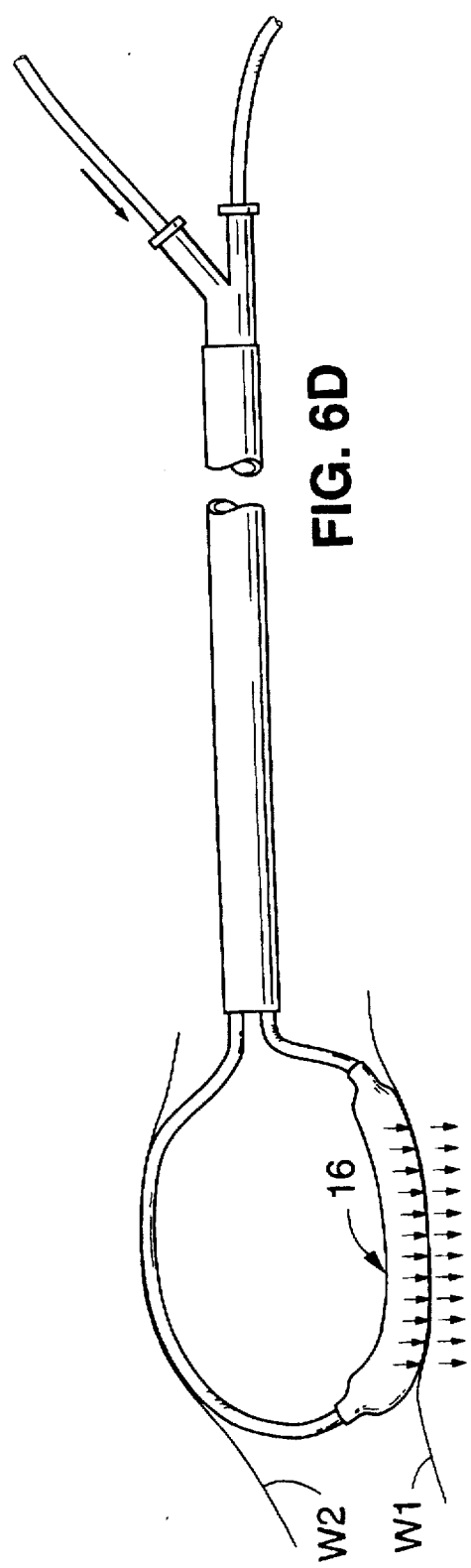

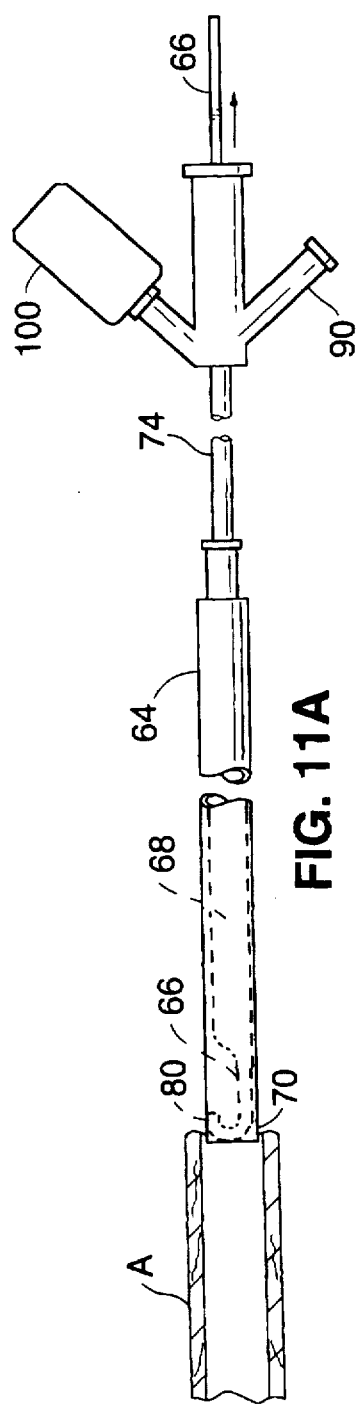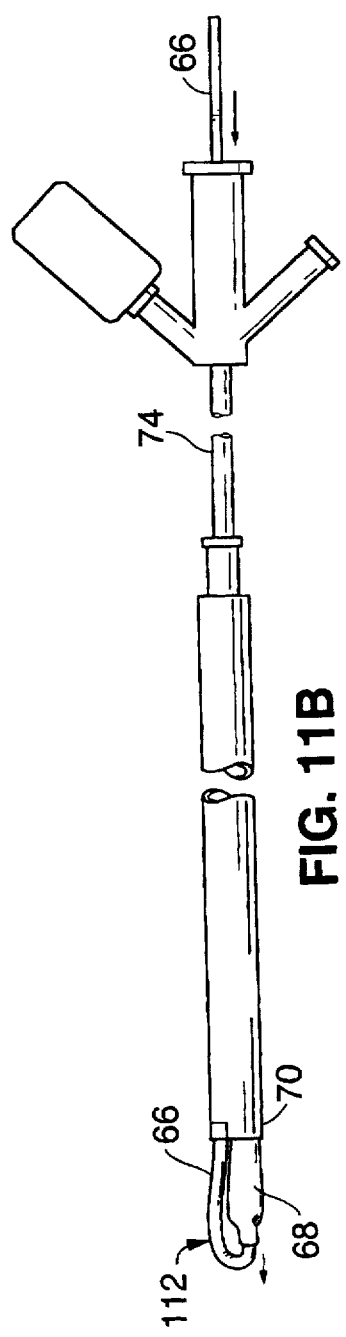
FIG. 11A
FIG. 11B

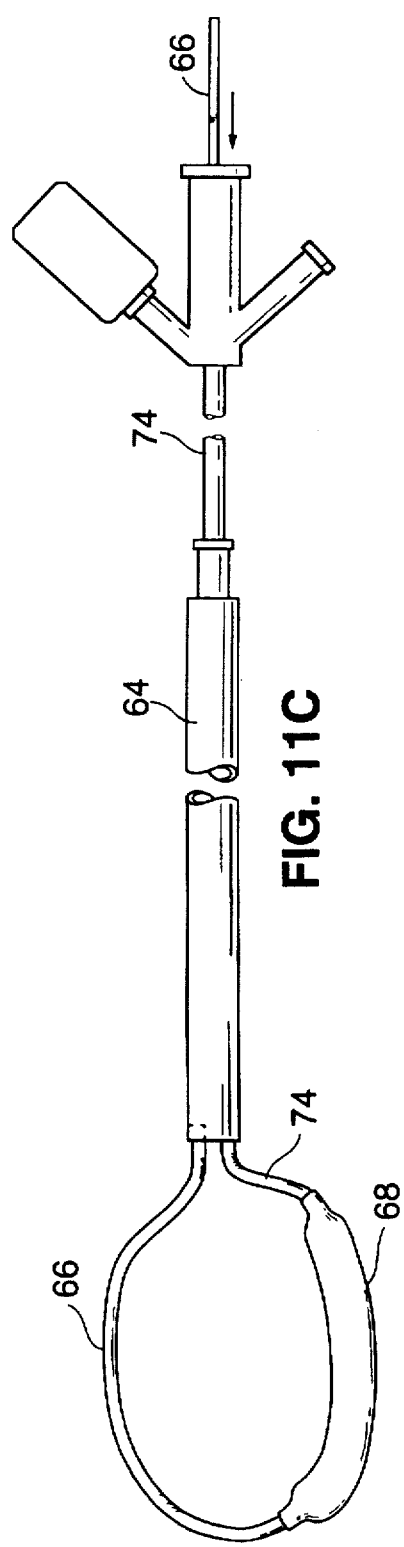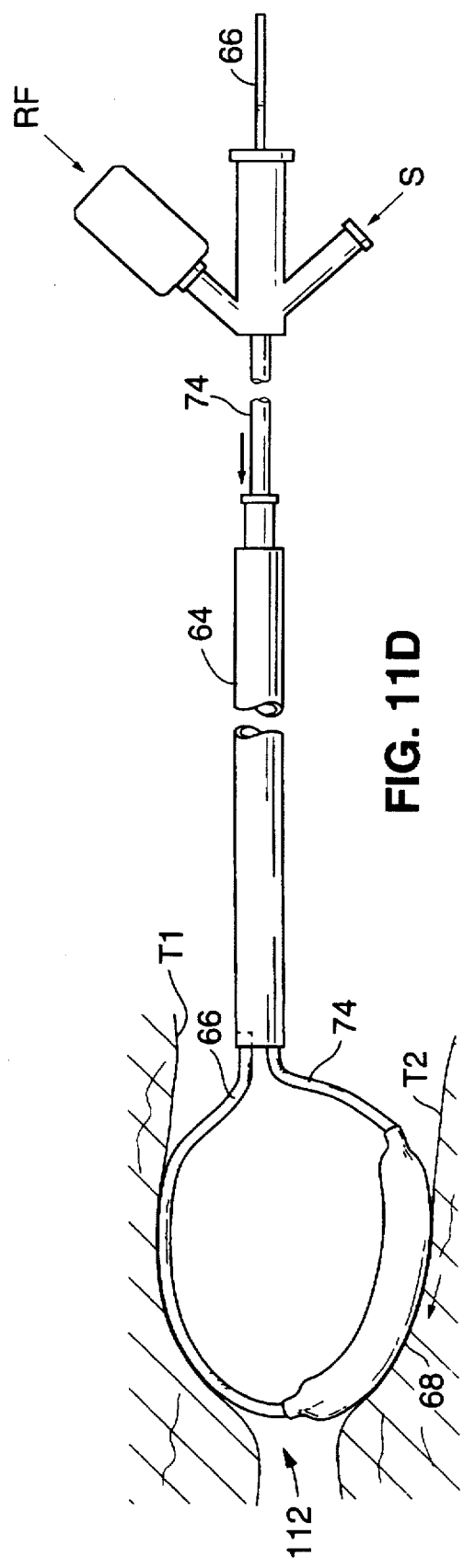

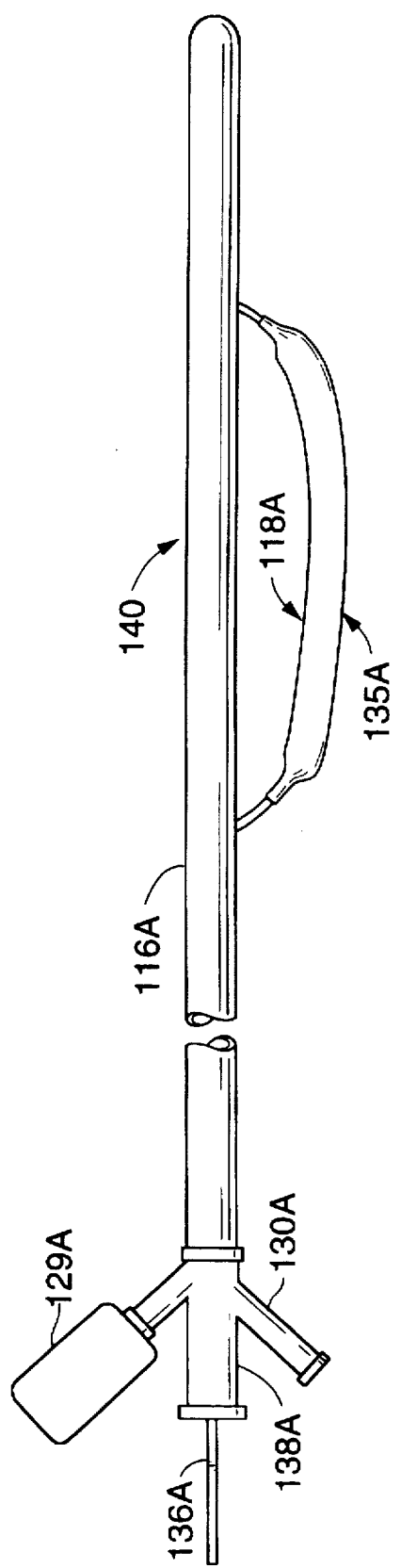
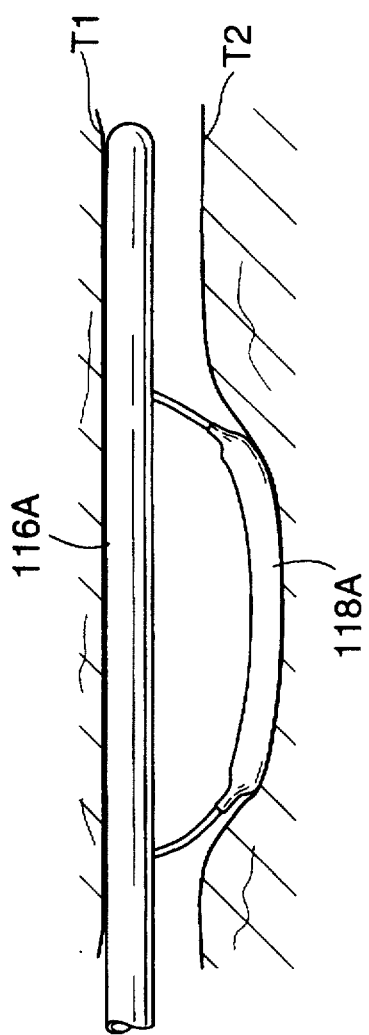

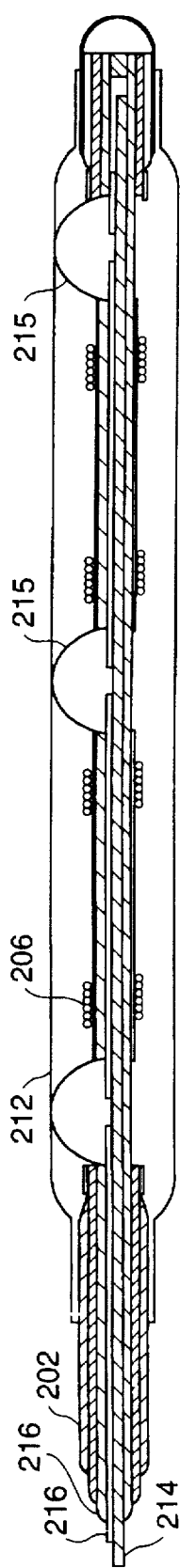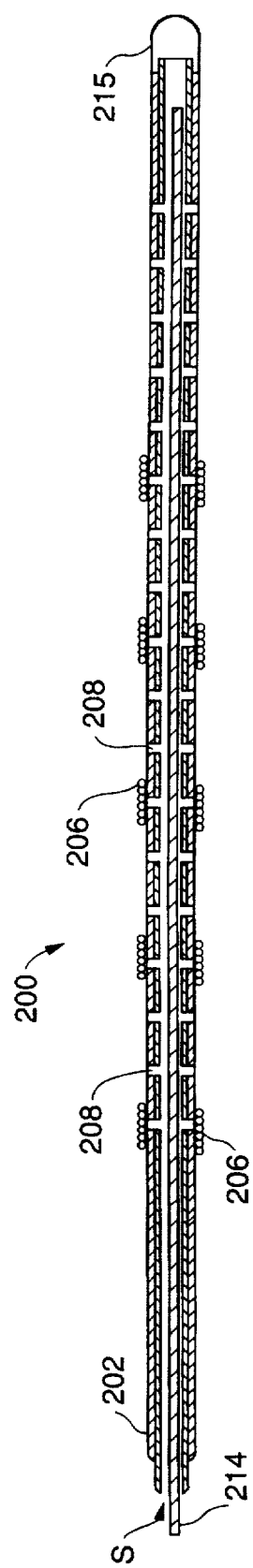
FIG. 16
FIG. 17

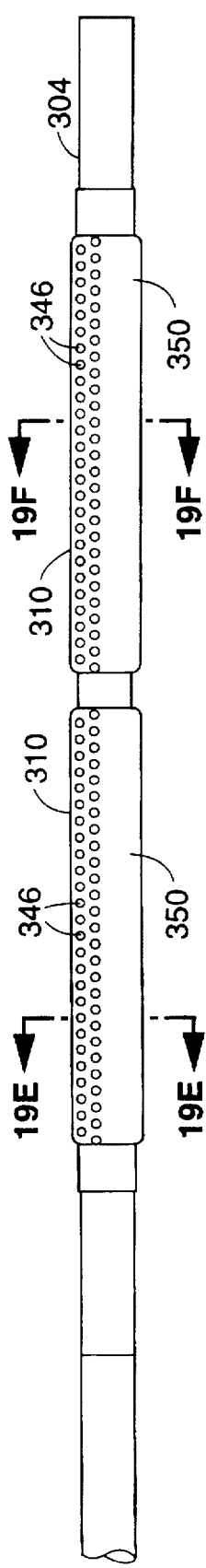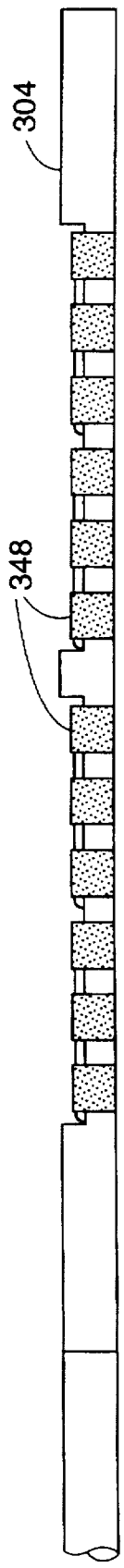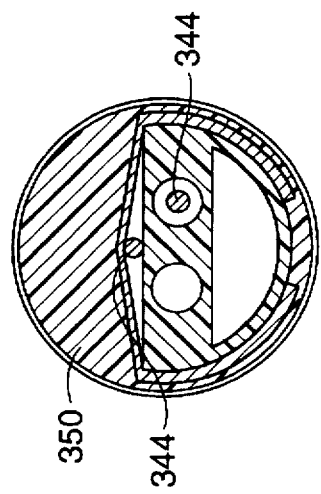

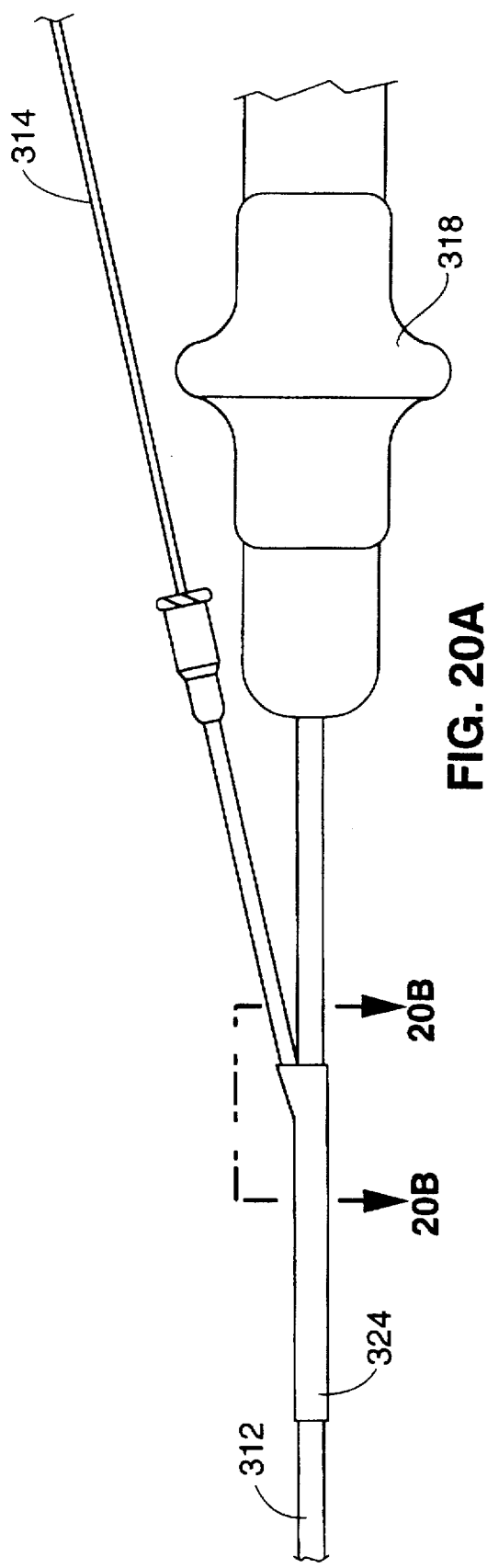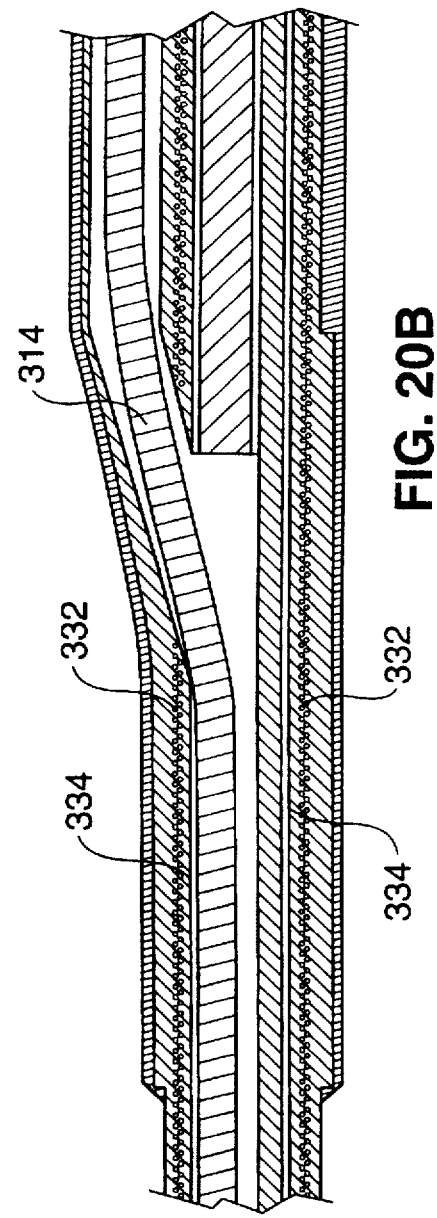

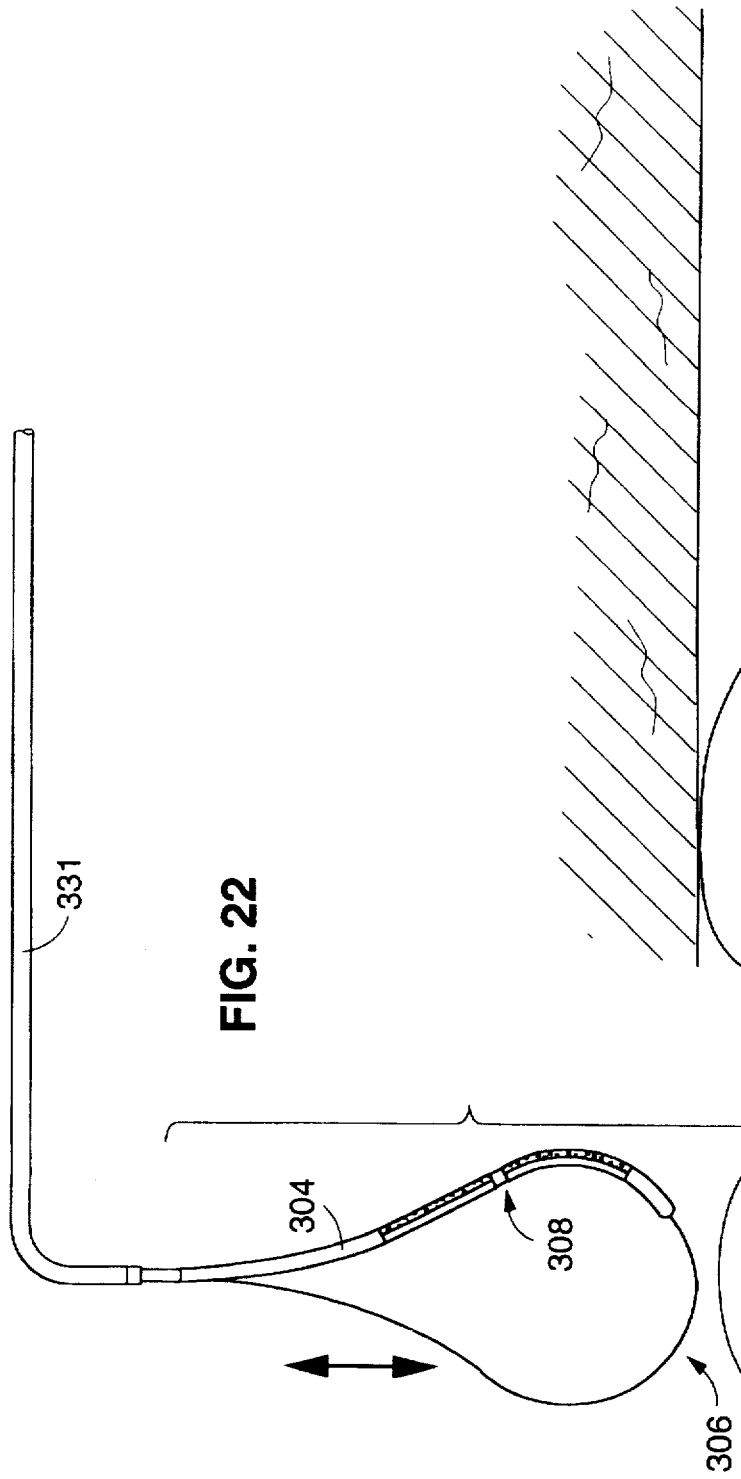
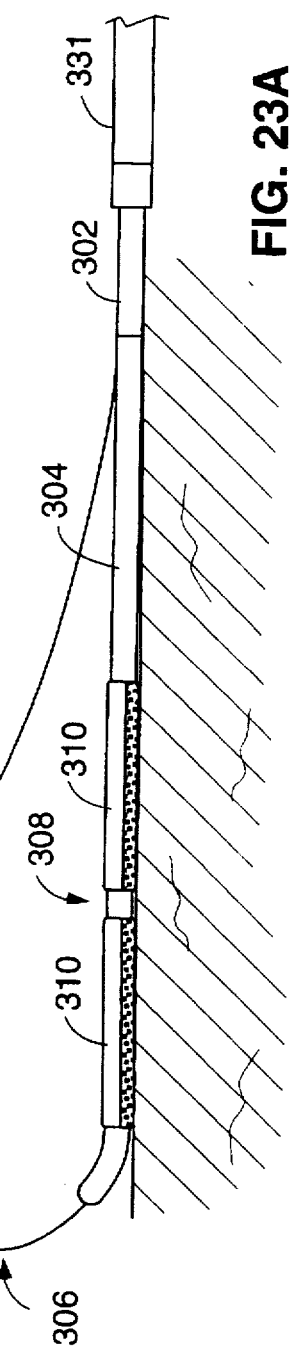
FIG. 22
FIG. 23A

DEFLECTABLE LOOP DESIGN FOR A LINEAR LESION ABLATION APPARATUS

This application is a continuation-in-part of application Ser. No. 08/611,656 filed on Mar. 6, 1996 now U.S. Pat. No. 5,800,482 entitled APPARATUS AND METHOD FOR LINEAR LESION ABLATION, by inventors Mark L. Pomeranz, Troy J. Chapman, Darren R. Sherman, and Mir Imran.

FIELD OF THE INVENTION

The present invention relates generally to the field of apparatuses and methods for ablating living tissue. In particular, the present invention relates to the field of devices and methods for creating lesions within the heart.

BACKGROUND OF THE INVENTION

Atrial fibrillation is a condition in the heart in which abnormal electrical signals are generated in the endocardial tissue to cause irregular beating of the heart. One method used to treat atrial fibrillation involves creating several long (i.e., approximately 2-10 cm) lesions on the endocardium within the atria. These lesions are intended to stop the irregular beating of the heart by creating barriers between regions of the atria. These barriers halt the passage through the heart of the abnormal currents generated by the endocardium. This procedure is commonly referred to as the "maze procedure" because it creates a maze of lesions design to block the passage of abnormal currents through the heart.

Existing procedures for forming such linear lesions include the highly invasive technique of opening the patient's chest and heart and forming linear incisions inside the atria. Naturally, the highly invasive nature of this procedure makes it a particularly high risk to the patient and necessitates extraordinarily long recovery time.

Other attempts have been made to form the linear lesions using ablation catheters fed into the heart via the patient's vessels (i.e., the arteries or veins). For example, one such procedure involves inserting into the atria a 7 French catheter having an ablation tip. Radio frequency (RF) energy is supplied to the tip as the tip is dragged across the endocardium, thereby burning linear lesions into the endocardium.

While often successful for forming linear lesions, the ablation tip of the catheter can sometimes lift off of the surface of the endocardium as it is dragged across the endocardium, creating one or more breaks in the lesion. Such breaks minimize the success of the ablation procedure by leaving a path through which current may travel during atrial fibrillation episodes.

Another type of existing RF linear lesion catheter has a plurality of spaced ring electrodes encircling the distal end of the catheter. Although ablation using such catheters has been successful, a large spacing (i.e., on the order of greater than 4 mm) must be provided between the ring electrodes to give the catheter adequate flexibility to move through the vessels and the heart. Unfortunately, however, leaving large spaces between the electrodes may prevent RF energy from being focussed at certain points along the catheter and may thereby produce regions in the linear lesion which are not sufficiently necrosed to prevent the passage of current during atrial fibrillation episodes. Additionally, blood may coagulate on the surface of the metal ring electrodes, which can prevent RF energy from reaching the endocardial tissue. Coagulum on the surface of the electrodes may present a safety hazard in that it may eventually fall off the electrode and into the patient's bloodstream, causing an embolic event.

Procedures and devices for forming linear lesions within the atria are therefore desired which will block the passage of current through the heart during atrial fibrillation episodes, as with the surgical incision procedure, but which utilize the less-invasive technique of a percutaneous catheter. Further desirable is a linear lesion catheter having the flexibility and maneuverability of the electrode tipped catheter but which generates a continuous lesion on the endocardium.

It is further desirable to improve the continuity and thus the effectiveness of linear lesions formed using ablation catheters by providing means by which a linear lesion catheter may be held securely against endocardial tissue during ablation, and by which electrical energy may be focussed from the ablation electrodes onto the endocardium.

SUMMARY OF THE INVENTION

The present invention is a catheter device for creating linear lesions in endocardial tissue or other body tissue. The catheter includes an elongate member having an ablation section at which a number of spaced apart electrodes are carried. An infusion tube is also carried by the elongate member. The infusion tube has a plurality of tiny holes positioned near the electrodes.

During use, the ablation section of the apparatus is positioned adjacent to the body tissue which is to be ablated. RF energy is delivered to the electrodes while saline or other conductive fluid is simultaneously delivered through the infusion tube. The conductive fluid passes out of the openings in the infusion tube and contacts the electrodes. The fluid also flows into contact with the body tissue, thereby improving the coupling of the RF energy from the electrodes to the tissue and improving the efficiency of the ablation of the tissue.

Utilizing a conductive liquid which is dispersed over the desired area as a mechanism for coupling RF energy to the tissue produces lesions having greater continuity (and thus fewer breaks through which current can pass during atrial fibrillation episodes) than lesions formed by prior art apparatus which rely solely on direct contact between the electrodes and the body tissue. The conductive liquid also cools the electrodes, decreasing the likelihood of thrombus formation on the electrodes and thus decreasing the chance of embolism.

In preferred embodiments, delivery of current to the tissue is further improved by surrounding the electrodes with foam material and by covering the foam with a substantially fluid impermeable covering having a number of tiny holes formed in it. Saline (or another conductive medium) flowing into the foam is uniformly dispersed within it, and then is focussed onto the body tissue as it passes through the holes in the covering.

Because the foam is deformable, it conforms the covering to the surface of the body tissue when the ablation section is positioned in contact with body tissue. Further, as saline infuses into the foam, it slightly expands the covering against the tissue thereby providing positive pressure between the covering and the body tissue. Certain of the embodiments are further provided with baffle wires that mechanically leverage the ablation section against the body tissue which is to be ablated. In such embodiments, the ablation section may be fixed or slidable on the baffle wire. Additional embodiments are also provided with features such as the use of a guide sheath and one or more pullwires which allow the ablation section to be more easily maneuvered.

BRIEF DESCRIPTIONS OF THE DRAWINGS

FIGS. 6A through 6D are a series of side elevation views of the linear lesion catheter of FIG. 1 illustrating operation of the device.

FIGS. 11A through 11D are a series of side elevation views of the linear lesion catheter of FIG. 7 illustrating operation of the device.

FIG. 12A is a side view of the alternative catheter.

FIG. 12B is a cross-sectional view of a distal portion of the alternative catheter taken along the plane designed 12B—12B in FIG. 12A.

FIG. 12C is a cross-sectional view of a proximal portion of the alternative catheter taken along the plane designed 12C—12C in FIG. 12A.

FIG. 14A is a side elevation view of a fourth embodiment of a linear lesion catheter according to the present invention.

FIG. 14C is a side elevation view of a portion of the catheter of FIG. 14A illustrating the manner in which the catheter secures the ablation section against endocardial tissue.

FIG. 16 is a cross-sectional side view of a sixth embodiment of a linear lesion catheter according to the present invention which is similar to the fifth embodiment but in which the foam support structure of the fifth embodiment has been replaced by inflatable support structures.

FIG. 17 is a cross-sectional side view of a seventh embodiment of a linear lesion catheter according to the present invention which is similar to the fifth embodiment but in which the foam support structure and covering have been removed.

FIGS. 19C and 19D are side views of the electrodes of the linear lesion catheter of FIG. 18.

FIGS. 19E and 19F are cross-sectional views of the ablation section of the linear lesion catheter of FIG. 18 taken along planes designated as 19E—19E and 19F—19F in FIG. 19C.

FIGS. 20A and 20B are side views of the portion of the linear lesion catheter of FIG. 18 wherein the baffle ribbon diverges from the main shaft.

FIG. 22 is an illustration of the linear lesion catheter of FIG. 18 within a guide sheath.

FIGS. 23A through 23C are a series of side elevation views of the linear lesion catheter of FIG. 18 which illustrate the operation of the device.

DETAILED DESCRIPTION OF EXEMPLARY EMBODIMENTS

Figure 1:
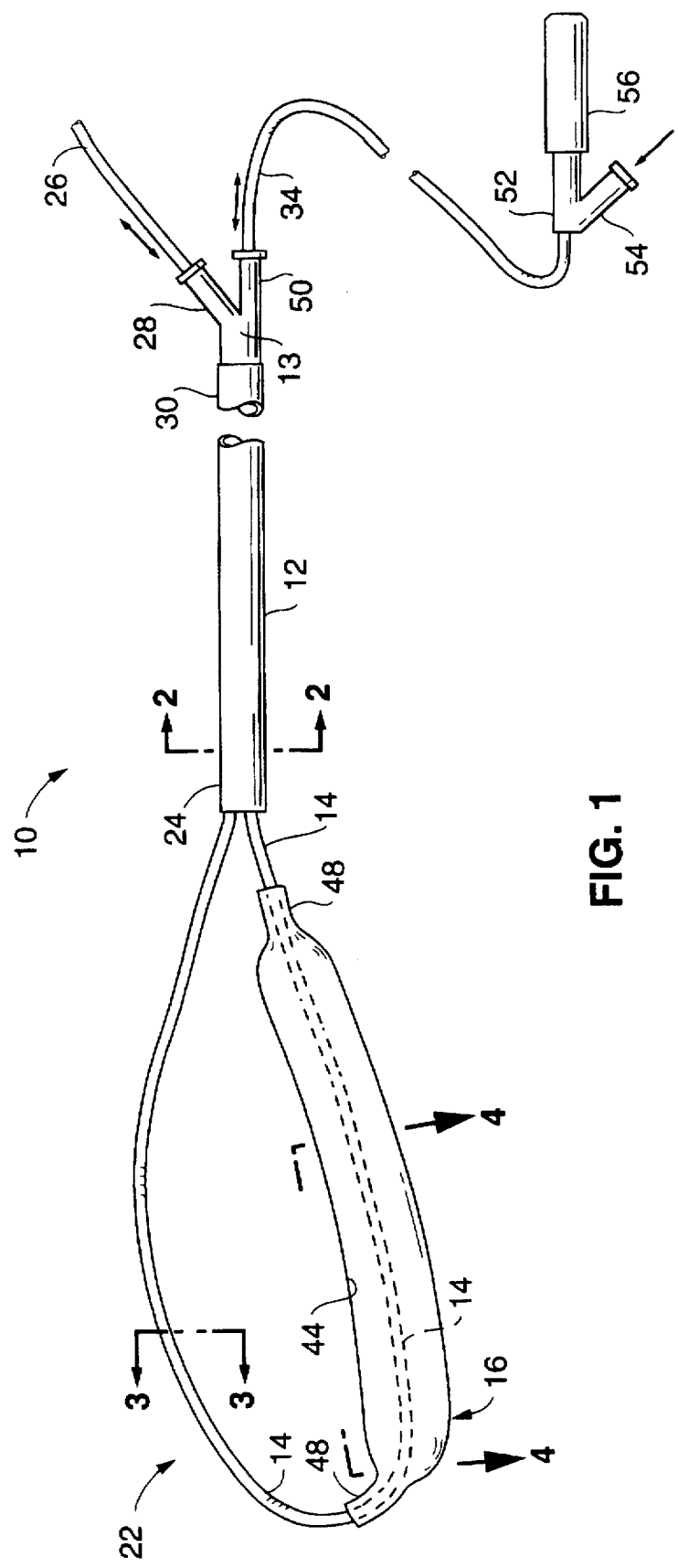
FIG. 1 is a side elevation view of a first embodiment of a linear lesion catheter according to the present invention.

A first embodiment of a linear lesion catheter 10 according to the present invention is shown in FIG. 1. The catheter 10 is comprised generally of a main shaft 12, a looped baffle wire 14 which extends through the main shaft 12 and which is extendable out of the distal end of the main shaft 12, and an ablation section 16 formed on the baffle wire 14. During use, the ablation section 16 is positioned against the target tissue to be ablated and which delivers RF energy to the tissue to cause ablation. It should be appreciated that other types of ablation elements may be substituted for the RF ablation elements described in this and the following embodiments. For example, ultrasound ablation elements or other conventional ablation tips may be used in combination with some or all of the other features of the invention described herein without departing from the scope of the present invention.

Figure 2:
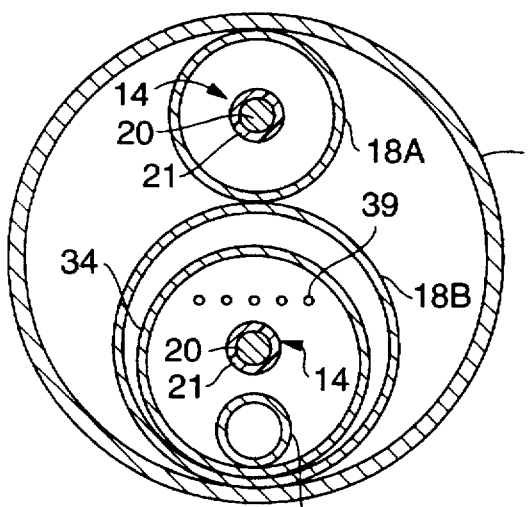
FIG. 2 is a cross-sectional view of the main shaft of the linear lesion catheter of FIG. 1, taken along the plane designated 2—2 in FIG. 1.

Referring to FIG. 2, main shaft 12 is an elongate shaft having a pair of lumens 18a, 18b extending from its proximal to its distal end. Although the main shaft 12 is substantially straight in this and the other embodiments described herein, it may alternatively have a curved profile at its distal end to facilitate contact between it and the target tissue to be ablated. Main shaft is preferably constructed of a thermoplastic polymer, polyamide ether, polyurethane or other material having similar properties. A stainless steel braid (not shown) is preferably embedded in the wall of the main shaft by means conventionally known in the art. The inclusion of the braid improves the torque characteristics of the main shaft 12 and thus makes the main shaft easier to maneuver through patient's vessels and heart. A connector 13 is attached to the proximal end of main shaft 12.

Figure 3:
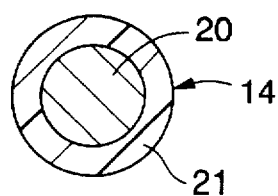
FIG. 3 is a cross-sectional view of the baffle wire of the linear lesion catheter of FIG. 1, taken along the plane designated 3—3 in FIG. 1.

Referring to FIG. 3, baffle wire 14 is an elongate length a metallic core wire 20 encased in thin shrink tubing 21 or other flexible tubing such as polyolefin, thermoplastic polymer, polyamide ether (nylon), silicone, or polyurethane. Metallic core wire 20 extends the length of the shaft and may be formed of, for example, stainless steel or shape memory metal such as Nitinol. The baffle wire 14 may alternatively be formed of a more rigid material such as conventional braid tubing, in which case the core wire 20 may be eliminated.

Baffle wire 14 extends through each of the lumen 18a, 18b in the main shaft 12 and forms a loop 22 (FIG. 1) adjacent to distal end 24 of the main shaft 12. Baffle wire 14 includes a first end 26 which extends from a port 28 in connector 13. A second end 32 of baffle wire 14 lies within tubing 34 which extends from proximal end 30 of the main shaft and which will be described in detail below.

Figure 4:
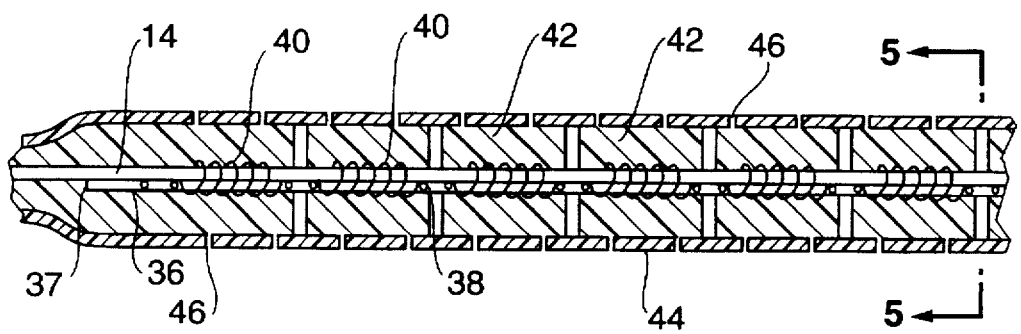
FIG. 4 is a cross-sectional view of the ablation section of the linear lesion catheter of FIG. 1, taken along the plane designated 4—4 in FIG. 1.
Figure 5:
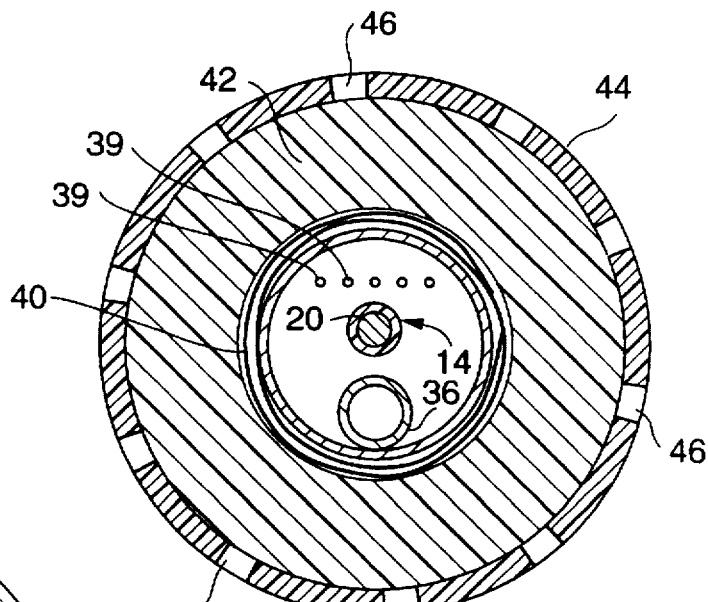
FIG. 5 is a cross-sectional view of the ablation section of the linear lesion catheter of FIG. 1, taken along the plane designated 5—5 in FIG. 4.

Ablation section 16 of the catheter 10 is shown in cross-sectional view in FIGS. 4 and 5. Referring to FIG. 5, ablation section 16 includes a small diameter (i.e., approximately 0.5 mm diameter) fluid infusion tube 36 which extends adjacently to a portion of baffle wire 14. Infusion tube 36 includes a sealed distal end 37 and it extends proximally through the main shaft 12 and the tubing 34. A plurality of spaced holes 38 extend along the portion of the infusion tube 36 which lies at the ablation section 16.

A plurality of lead wires 39 (FIG. 5), which are preferably formed of copper, extend adjacently to the infusion tube 36 and the baffle wire 14. Referring to FIG. 4, each lead wire 39 has a distal end coiled around the infusion tube 36, baffle wire 14, and other lead wires 39 to form a coil electrode 40. The proximal portions of the lead wires 39 extend through the main shaft 12 and tubing 34 and are coupled to an electrical adapter as will be described below. The portions of the lead wires 39 which are disposed within the ablation section 16 are not insulated from one another, while the portions of the lead wires 39 which lie within the main shaft 12 and tubing 34 are preferably insulated from one another by shrink tubing or other means.

Other types of electrodes may alternatively be used in this and the other embodiments described herein. For example, ring electrodes may be utilized, or spaced conductive strips or bands may be formed on the surface of the baffle wire, or wire braids or other conductive material may be helically wound around the baffle shaft. The electrodes may also be formed from conductive wires or ribbons, each of which is covered by an insulated coating. An example of such wires (in an uncoiled form) is designated 94a in FIG. 12D and is described in the description accompanying FIG. 12D. The wire 94a is an 0.005" diameter wire which is provided with exposed electrode regions 96a that are stripped of insulative material. Such flattened wires or ribbons may be advantageous in that they produce RF energy electric field lines which are not concentrated at the edges of the ribbons, but are instead dispersed along the entire length of the ribbon.

Deformable members, or foam support segments 42 surround the electrodes 40. These segments 42 are formed of open cell polyurethane, cotton-like material, open-cell sponge, hydrogels, or other foam-like materials or materials which are permeable by conductive fluids and which exhibit some compressibility. The deformable member need not be segmented but it has been found that RF energy is more effectively channeled to the cardiac tissue by providing the foam in segments rather than in a continuous piece.

The support segments 42 are preferably foam tubes which during manufacture are slipped over the baffle wire 14 into position over the electrodes. Alternatively, foam sheets may be wrapped around the electrodes to form tubes around the electrodes, and the overlapping sides of each sheet glued together to maintain each sheet in a tubular configuration.

The support segments 42 are enclosed within a covering 44 formed of heat shrink polyethylene, silicone, or other polymeric materials having a plurality of small holes 46 or perforations formed in it. The covering 44 is preferably held in place by heating ends 48 (FIG. 1) of the covering to cause the heat shrink material to melt onto the baffle wire 14. Covering 44 may also be a dip coating formed on the foam surface.

A number of functions are performed by the foam 42 and covering 44 during use of the device. During use, the ablation section 16 of the device is positioned in contact with the region of the endocardium which is to be ablated. The foam provides structural support for the covering and facilitates contact between the covering and endocardial surface by compensating for features on the endocardial surface which are not smooth. It should therefore be appreciated that in this and the below described embodiments, the foam support segments may be replaced by other mechanical means which give structure integrity to the covering 44. For example, inflatable balloons may be positioned within the covering and inflated to push the covering outwardly against the endocardial surface. Alternatively, the covering may be positioned over plastic or metallic spring structures.

Further, as described in detail below, RF energy is delivered to the endocardium by a conductive path through the saline which flows through the foam and out of the covering onto the endocardium. The foam 42 helps the saline to flow evenly through and out of the covering and therefore facilitates transmission of RF energy to the endocardium.

The plurality of tiny holes 46 formed in the covering 44 serve as the conduit through which saline passes from the foam to the endocardium. The fluid flow through the holes focuses the RF energy onto the tissue. The pattern in which the holes are arranged is selected to insure infusion of saline and delivery of RF energy to the underlying tissue even if the ablation section 16 should rotate during use. The distribution of holes formed in the covering should be limited to that which will create a continuous transmural linear lesion over the desired ablation surface. It has been found desirable to use four rows of 0.007" diameter holes spaced 1.0 mm apart over the length of the active region of the ablation section, to give approximately 40 such holes per centimeter over the active region. Six rows of holes (or 60 holes per centimeter) is also believed to give good results.

It may also be desirable to arrange the holes so that they extend only along one side of the covering (i.e., the side which, during use, will be positioned against the target ablation site) in order to prevent RF energy from being lost into the blood pool. See, for example, holes 110a in FIG. 12D. It should be appreciated, however, that many hole sizes and patterns may be utilized without departing from the scope of the present invention.

The covering 44 helps to prevent blood from entering the ablation section, and the positive outward flow of saline from the covering reduces the likelihood of thrombus buildup at the ablation site.

Referring to FIG. 1, tubing 34 (which, as shown in FIG. 2, contains baffle wire 14, leads 39, and infusion tube 36 within it) extends through the main shaft 12 from the distal end 24 of the main shaft, and it exits proximal end 30 of main shaft via a port 50 in connector 13. Tubing 34 is slidably disposed within main shaft 12 and connector 13.

Tubing 34 (now containing only leads 39 and infusion tube 36) is joined at its proximal end to a second connector 52. Alternatively second connector 52 may be a handle. Tubing 34 terminates at connector 52, and the infusion tube 36 and lead wires 39 which are within it (see FIG. 2) diverge from one another such that infusion tube 36 is fluidly coupled with a fluid port 54 in connector 52 and such that lead wires 39 are electrically coupled to a female adapter 56. The second end 32 of baffle wire 14 located at connector 52 does not extend into the fluid port 54 or the female adapter 56 but instead terminates at, and is fixed within, connector 52.

Alternatively, connector 13 may be eliminated so that tubing 34 containing baffle wire 14, leads 39, and infusion tube 36 is joined at its proximal end to either a connector or a handle. In this version, the connector would be as described above except for the presence of an additional port to accommodate the first end 26 of baffle wire 14. However, use of a second connector is preferred since the placement of ablation section 16 is more easily maneuvered when the first end 26 of baffle wire 14 exits from a different port than infusion tube 34 and leads 39.

Female adapter 56 is preferably configured to be coupled to a multi prong male adapter 58 (FIG. 6A) which is electrically coupled to a conventional RF generator (designated 60 in FIG. 6A) such as Model 8002 RF Generator which is available from Cardiac Pathways Corporation, Sunnyvale, Calif. Each lead wire 39 coupled to the female adapter preferably terminates in a socket which is separate from the other sockets in the female adapter and which is configured to mate with a corresponding prong of the male adapter. Thus, for example, if the linear lesion catheter is provided with six electrodes 40 (FIG. 2), there will be six leads 39, each extending from one of the electrodes 40, and there will be at least six sockets in the female adapter which correspond to six prongs in the male adapter.

Operation of the first embodiment 10 of a linear lesion ablation catheter 10 according to the present invention will next be described. Prior to beginning the procedure, tubing 34 and end 26 of baffle wire 14 are pulled in a proximal direction, as indicated by arrows in FIG. 6A, to withdraw the loop 22 inside distal end 24 of main shaft 12. Female adapter 56 is connected to a male adapter 58 which is coupled to a source 60 of RF energy. A conventional grounding patch or other grounding device is attached to the patient's body.

With the loop 22 inside main shaft 12, main shaft 12 is threaded through a patient's vessels and into the heart using conventional techniques. Once distal end 24 of main shaft 12 is positioned within the appropriate chamber of the heart, end 26 of baffle wire 14 and/or the tubing 34 is advanced distally to push the loop 22 out of distal end 24 of main shaft 12 (FIG. 6B). The height, location and size of the loop 22 may be adjusted to position the ablation section 16 of the apparatus against the desired surface within the heart chamber and to maintain contact between the ablation surface of the catheter and the target surface within the heart chamber. These adjustments can be made by moving end 26 and/or tubing 34 distally or proximally as needed, and also by rotating the main shaft 12.

For example, tubing 34 may be moved distally to advance ablation section 16 and to thereby increase its curvature as shown in FIG. 6C, if such curvature will conform the ablation section 16 to the cardiac tissue T.

Moreover, loop 22 is preferably positioned within the heart such that ablation section 16 is leveraged against a chamber wall W1 by the action of the opposite side of the loop 22 against an opposing chamber wall W2 as in FIG. 6D. Pressing the ablation section 16 against the endocardium in this manner helps the ablation section to conform to the surface of the endocardium and thus helps ensure that sufficient contact is made between the ablation section and the endocardium. Good contact between the ablation section and the underlying tissue is essential to the creation of a continuous transmural lesion.

Delivery of RF energy to the endocardial tissue is commenced once ablation section 16 is in contact with the desired region of the endocardial surface. RF energy from RF generator 60 is delivered to electrodes 40 via leads 39. At the same time, conductive fluid, such as saline S (FIG. 6A), is directed into port 54 and through infusion tube 36. It may also be desirable to begin to apply positive fluid pressure even before RF ablation is commenced, in order to prevent blood accumulation in or on the covering.

The saline passes through holes 38 in the infusion tube 36, then through the foam 42, and out of the covering 44 via holes 46. As the saline moves from the holes 38 to the exterior of the covering, it creates a conductive path (for passage of the RF energy) between the electrodes and the endocardium (see arrows in FIG. 6D). The RF energy travels along this conductive path from the electrodes, through the foam and the holes in the covering, and then into the tissue. Once a lesion has been formed at the target spot, the catheter 62 may be repositioned within the selected chamber of the heart and additional lesions formed.

Although it is preferred to utilize the conductive fluid or saline in a manner in which the conductive fluid creates a conductive path between the electrodes and the target tissue, saline may alternatively or additionally be utilized in the present invention to cool the ablation electrodes.

A second embodiment of a linear lesion catheter 62 is shown in FIGS. 7–11B. Like the first embodiment, in the second embodiment the ablation section is positioned on a baffle loop at the distal end of the apparatus. The second embodiment differs from the first, however, in that in the second embodiment the ablation section is slidable over the baffle wire. Thus, once the catheter has been inserted into a heart chamber and the loop has been formed to a desired size, the position of the ablation section on the loop may be adjusted to position the ablation section at the target ablation location.

Catheter 62 generally includes a main shaft 64, a baffle ribbon 66 which has one end fixed to the distal end of the main shaft 64 and another end extending through main shaft 64, and an ablation section 68 slidably received on the baffle ribbon 66. The ablation section 68 preferably has a length of approximately 2–10 cm and an outer diameter of approximately 3–5 mm.

Figure 7:
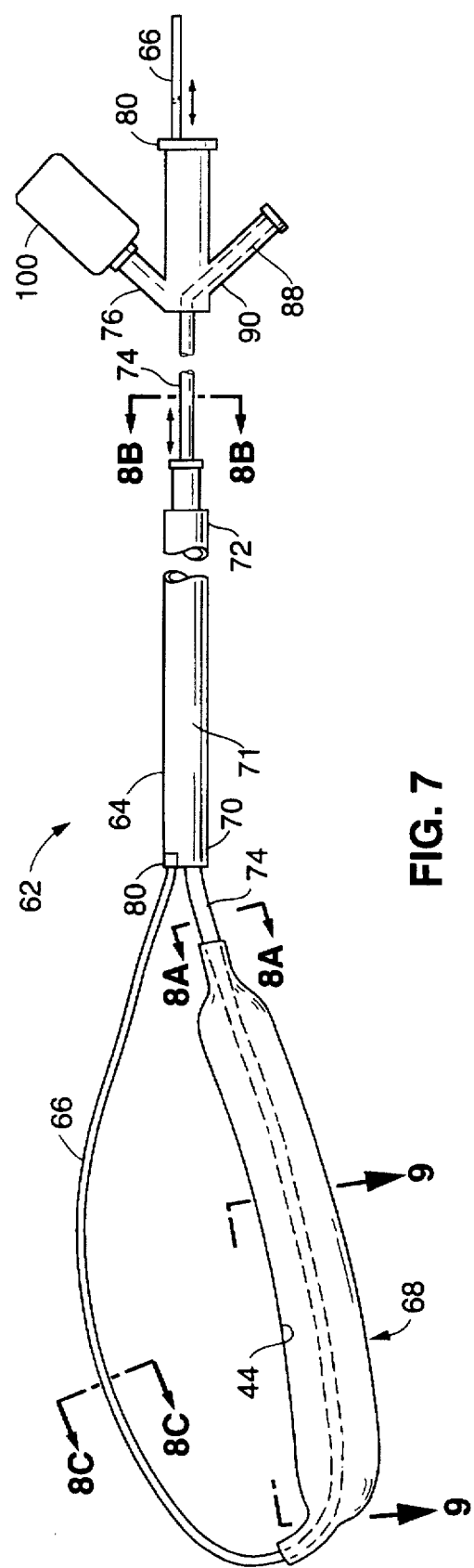
FIG. 7 is a side elevation view of a second embodiment of a linear lesion catheter according to the present invention.

Referring to FIG. 7, main shaft 64 includes a distal end 70 and a proximal end 72. The main shaft 64 is preferably a single lumen length of tubing constructed of a thermoplastic polymer, polyamide ether, polyurethane or other material having similar properties. The diameter of main shaft 64 is preferably approximately 9–11 French (approximately 3–4 mm). A stainless steel braid (not shown) is preferably embedded in the wall of the main shaft by means conventionally known in the art. The inclusion of the braid improves the torque characteristics of the main shaft 64 and thus makes the main shaft easier to maneuver through a patient's vessels and heart. A Teflon® lining (not shown), also conventional in the art, preferably lines the interior wall of the main shaft 64 to cover the wire braid. To minimize tissue trauma as the main shaft 64 is fed through a patient's vessels and heart during use, the braid is preferably absent from the first several centimeters at the distal tip 71 of the main shaft. This leaves the tip 71 sufficiently flexible to yield when advanced against obstacles within the vessels and heart.

Figure 8C:
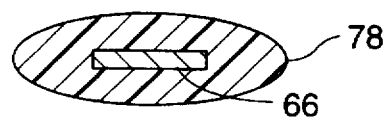
FIG. 8C is a cross-sectional view of the baffle wire of the catheter of FIG. 7, taken along the plane designated 8C—8C in FIG. 7.
Figure 8A:
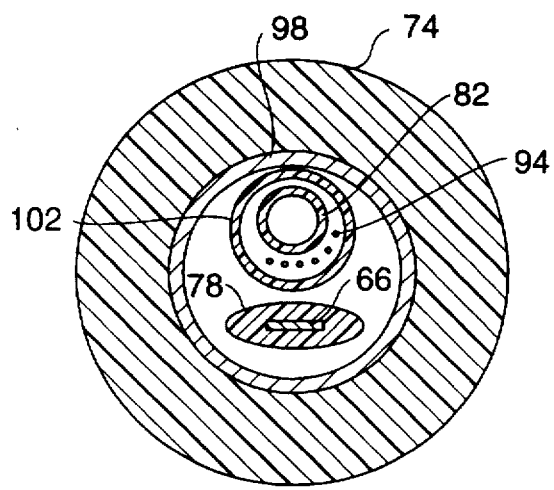
FIG. 8A is a cross-sectional view of a proximal portion of the tubing of the catheter of FIG. 7, taken along the plane designated 8A—8A in FIG. 7.
Figure 8B:
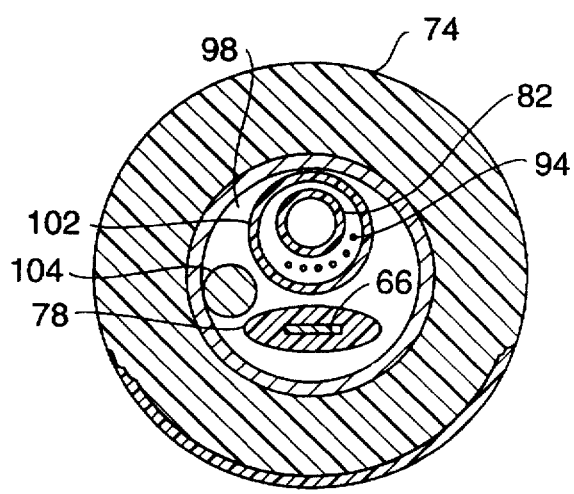
FIG. 8B is a cross-sectional view of a proximal portion of the tubing of the catheter of FIG. 7, taken along the plane designated 8B—8B in FIG. 7.

Referring to FIGS. 7, 8A and 8B, tubing 74, which is preferably made of a thick walled heat shrink tubing or thermoplastic polymer, is slidably received within main shaft 64 and is extendable from the distal end and proximal ends 70, 72 of the main shaft 64. A connector 76 is attached to the proximal end of tubing 74.

Baffle ribbon 66 extends through a lumen 78 in the tubing 74 and is preferably covered with a Teflon® coating. As shown, baffle ribbon 66 preferably has a substantially flat cross-section (i.e., rectangular or oblong). This prevents the baffle ribbon 66 from rotating about its longitudinal axis during use.

Baffle ribbon 66 has a distal end 80 which is secured to the distal end 70 of main shaft 64 as shown in FIG. 7. Baffle ribbon 66 extends through the ablation section 68 of the device as will be described below, enters the distal most portion of tubing 74 (see FIG. 8A), and extends through the entire length of the tubing 74 (see FIG. 8B). It further extends through connector 76 attached to the proximal most end of the tubing 74 and extends freely out of an opening in the proximal most end 80 of the connector (see FIG. 7).

Figure 9:
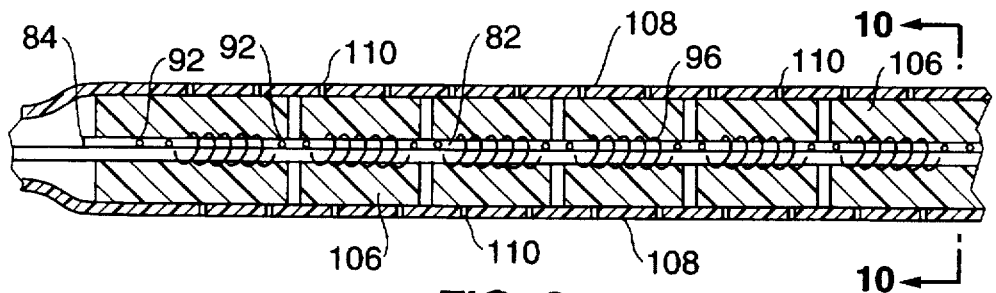
FIG. 9 is a cross-sectional view of the ablation section of the catheter of FIG. 7, taken along the plane designated 9—9 in FIG. 7.

Referring to FIG. 9, an infusion tube 82 extends through the ablation section 68 and through the tubing 74. Infusion tube 82 includes a sealed distal end 84 and a proximal end 88 fluidly coupled with a fluid port 90 formed in connector 76. A plurality of spaced holes 92 extend through the portion of the infusion tube 82 positioned at the ablation section 68 of the device.

Figure 10:
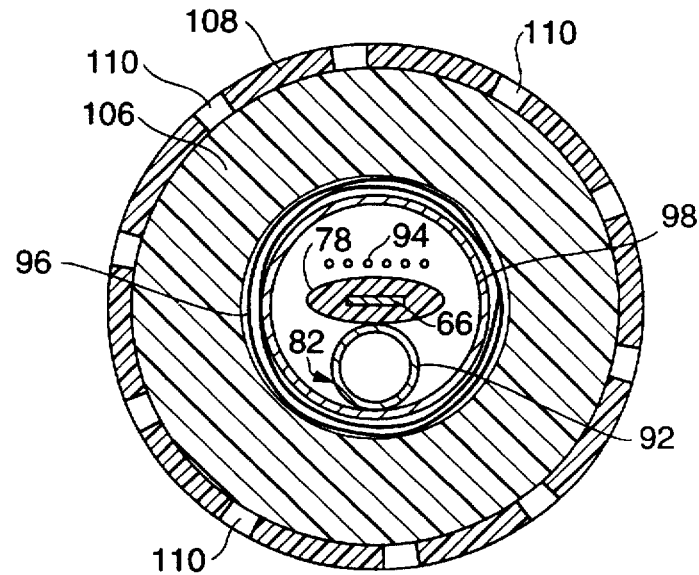
FIG. 10 is a cross-sectional view of the ablation section of the catheter of FIG. 7, taken along the plane designated 10—10 in FIG. 9.

A plurality of lead wires 94 (FIGS. 8A, 8B and 10), which are preferably formed of copper, extend through ablation section 68 and further extend through tubing 74, adjacent to the infusion tube 82. As can be seen in FIG. 10, at the ablation section 68 of the apparatus the lead wires 94, infusion tube 82, and the lumen that baffle ribbon 66 rides in are encased in thin walled polyethylene heat shrink tubing 98 (not visible in FIG. 9). Each lead wire 94 has a distal end which pokes through the shrink tubing 98 and is coiled to form a coil electrode 96 around the shrink tubing 98 and thus the infusion tube 82, the baffle ribbon 66, and the lead wires which are within it (see FIG. 10). Each of the wires 94 passes through the shrink tubing 98 at a different point along the length of the ablation section 68 such that the electrode coils 96 are spaced from one another. The proximal portions of the lead wires 94 pass through the tubing 74 and are electrically coupled to a female adapter 100 as described with respect to the first embodiment. The portions of the lead wires 94 which are disposed within the ablation section 68 are not insulated from one another, while the portions of the lead wires 94 which lie within the tubing 74 are preferably insulated from one another by shrink tubing or other means.

As can be seen in FIGS. 8A and 8B, the portions of the infusion tube 82 and lead wires 94 which are disposed within the tubing 74 are bundled together using thin walled polyethylene heat shrink tubing 102, whereas the portion of the baffle ribbon 66 lying within the tubing 74 is preferably not bundled within the tubing 102. A stiffening wire 104 extends through a proximal portion of the tubing 74 to facilitate manipulation of the catheter 62 within a patient's vessels and heart. Stiffening wire 104 has a proximal end (not shown) which is secured to connector 76, and an unsecured distal end (not shown) located proximally of distal tip 71 of main shaft 64 (compare FIGS. 8A and 8B).

Referring again to FIGS. 8A, 8B and 10, it can be seen that the same shrink tubing 98 which, at the ablation portion 68 (FIG. 10) of the device, encloses the leads 94, the lumen 78 within which the baffle ribbon 66 rides, and fluid lumen 82 also encloses tubing 102 (including infusion tube 82 and lead wires 94 which are within it), the lumen 78 within which the baffle ribbon 66 rides, and the stiffening wire 104 which are enclosed within the tubing 74. Moreover, it should be understood that during manufacture the thick walled tubing 74 becomes melted onto the underlying tubing 98 and thus prevents sliding of the shrink tubing 98 within the tubing 74.

Referring to FIGS. 9 and 10, support segments 106 formed of open cell polyurethane or other foam material are positioned to surround the electrode coils 96. The foam need not be segmented but as described below it has been found that RF energy is more effectively channeled to the cardiac tissue by providing the foam in segments. As described with respect to the first embodiment, the support segments 106 are preferably foam tubes which during manufacture are slipped over the baffle ribbon 66 and into position over the electrodes.

The support segments 106 are enclosed within a covering 108 formed of heat shrink polyethylene or other polymeric material and preferably held in place by melting the distal and proximal ends of the covering onto the underlying structures.

A plurality of tiny holes 110 are formed in the covering 108 and serve as the conduit through which saline passes from the foam to the endocardium. The pattern in which the holes are arranged is thus selected to insure infusion of saline and deliverance of RF energy to the underlying tissue even if the ablation section 68 should rotate during use. Because the holes focus the RF energy onto the tissue, it is preferable to limit the number of holes formed in the covering to that which will create a continuous transmural linear lesion.

Operation of the preferred catheter 62 according to the present invention will next be described. Prior to beginning the procedure, baffle ribbon 66 is pulled in a proximal direction to withdraw its distal portion as well as the ablation section 68 inside distal end 70 of main shaft 64. See FIG. 6A. Female adapter 100 is connected to a male adapter which is coupled to a source of RF energy as described above with respect to the first embodiment.

Once the ablation section 68 and the distal portion of the baffle ribbon 66 are inside main shaft 64, the main shaft 64 is threaded via a patient's vessels (one of which is designated A in FIG. 11A) into the heart using conventional techniques. Once distal end 70 of main shaft 64 is positioned within the appropriate chamber of the heart, the proximal end of baffle ribbon 66 is advanced distally as shown in FIG. 11B. Because distal end 80 of baffle ribbon 66 is fixed to the main shaft 64, distal movement of the baffle ribbon causes it to form a loop 112 with itself. Additional distal movement of the baffle ribbon 66 increases the size of the loop 112 as shown in FIG. 11C. Deployment of the baffle ribbon 66 continues until the loop 112 is of sufficient size that it fills the heart chamber (i.e., such that both ablation section 68 and the side of the loop 112 opposing the ablation section are in contact with opposition regions T1 and &2 of endocardial tissue). Next, the position of the ablation section 68 along the baffle wire 66 may be adjusted by sliding tubing 74 in a proximal or distal direction (distal sliding is indicated in FIG. 11D), to cause tubing 74 and thus inner shrink tube 98, to slide. Because the baffle ribbon 66 is not secured within the tubing 74 and 98, the tubing 74, 98 and the elements encased within it (i.e., the infusion tube 82 and the lead wires 94) slide over the baffle ribbon 66 while the baffle ribbon remains in place.

As described with respect to the first embodiment, delivery of RF energy to the endocardial tissue is commenced once ablation section 68 has been positioned in contact with the desired region of the endocardial surface. RF energy from an RF generator is delivered to the coil electrodes 96 via leads 94 and is carried from the electrodes 96 to the endocardium by a conductive fluid, such as saline S (FIG. 11D). As with the previous embodiment, the saline is directed into infusion tube 82 (FIG. 10) by fluid port 90. The saline passes through the holes 92 in the lumen 36, and then through the support segments 106, and it subsequently travels out of the covering 108 via holes 110. As the saline moves from the holes 110 to the exterior of the covering, it carries the RF energy passed from the electrodes through the foam out of the covering and onto the endocardium. Once a lesion has been formed at the desired spot, the user may reposition the ablation section 68 by sliding it proximally or distally over the baffle wire 66 (with or without first repositioning the baffle wire 600 within the chamber of the heart) in order to position the ablation section for formation of additional lesions. Once the ablation section is repositioned, RF energy is delivered to the electrodes to form additional lesions or to increase the length of the previously formed lesion.

Figure 12A:
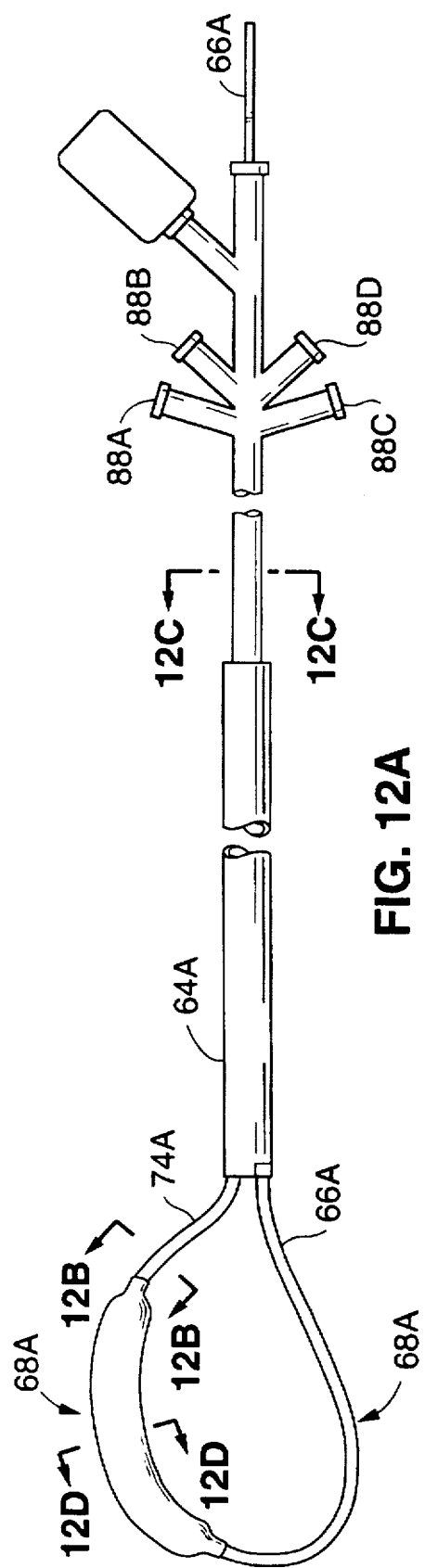
FIGS. 12A through 12C show a catheter which is similar to the catheter of FIG. 7 but which utilizes an alternative tubing configuration.
Figure 12B:
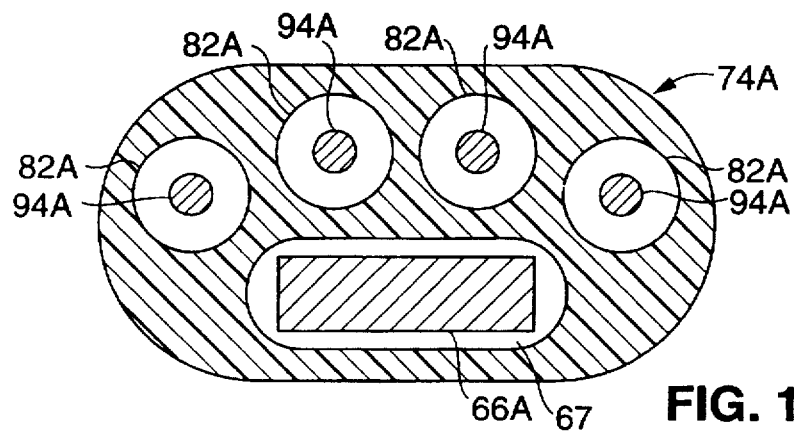
Figure 12C:
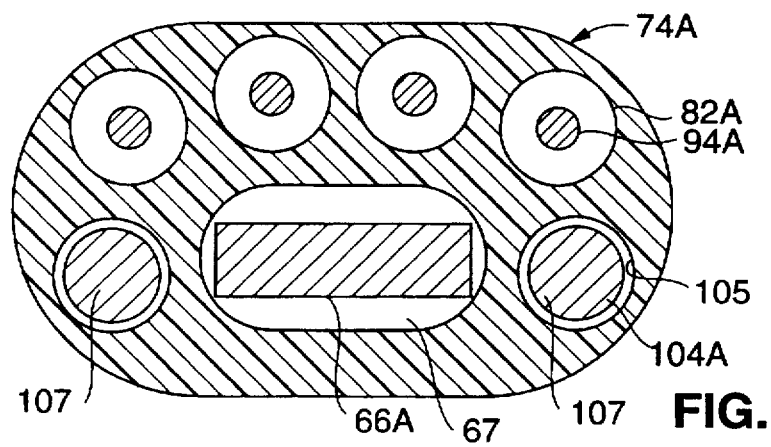

FIGS. 12A–12C show an alternative catheter according to the present invention. This is embodiment is like the embodiment of FIG. 7 in that the ablation section 68a is slidable over a baffle wire, but it differs primarily with respect to the configuration of the tubing 74a which extends through the shaft 64.

Figure 12D:
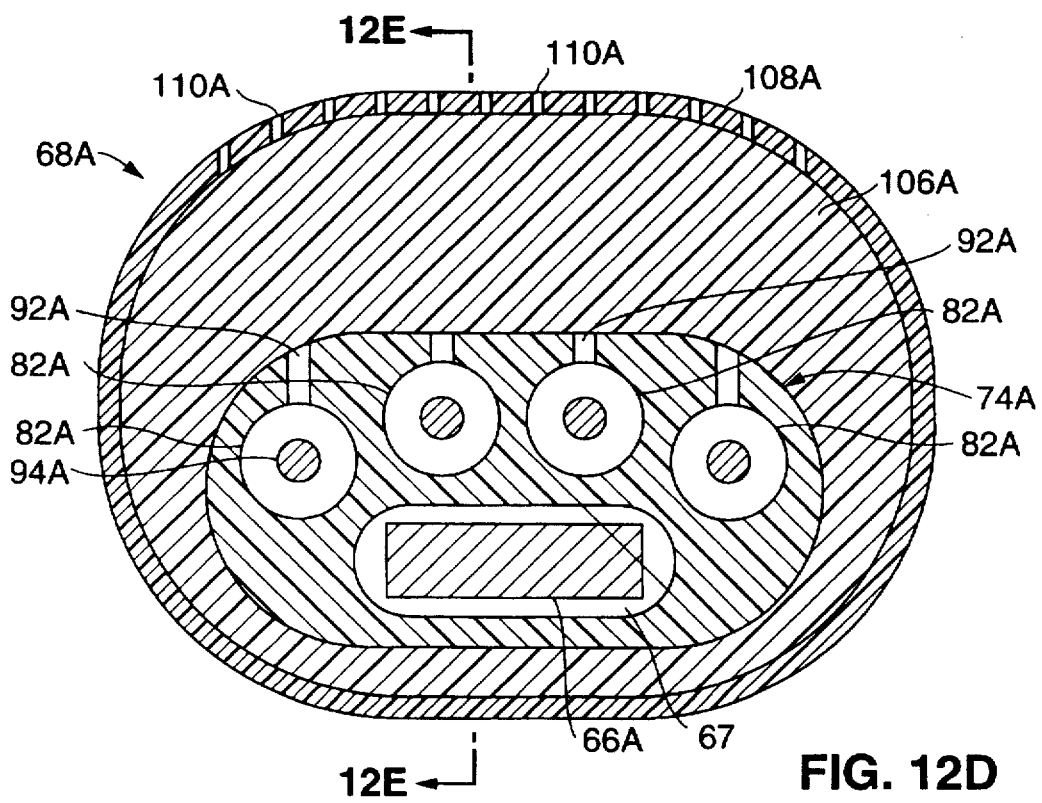
FIG. 12D is a cross-sectional view of the ablation section of the alternative catheter taken along the plane designed 12D—12D in FIG. 12A.
Figure 12E:
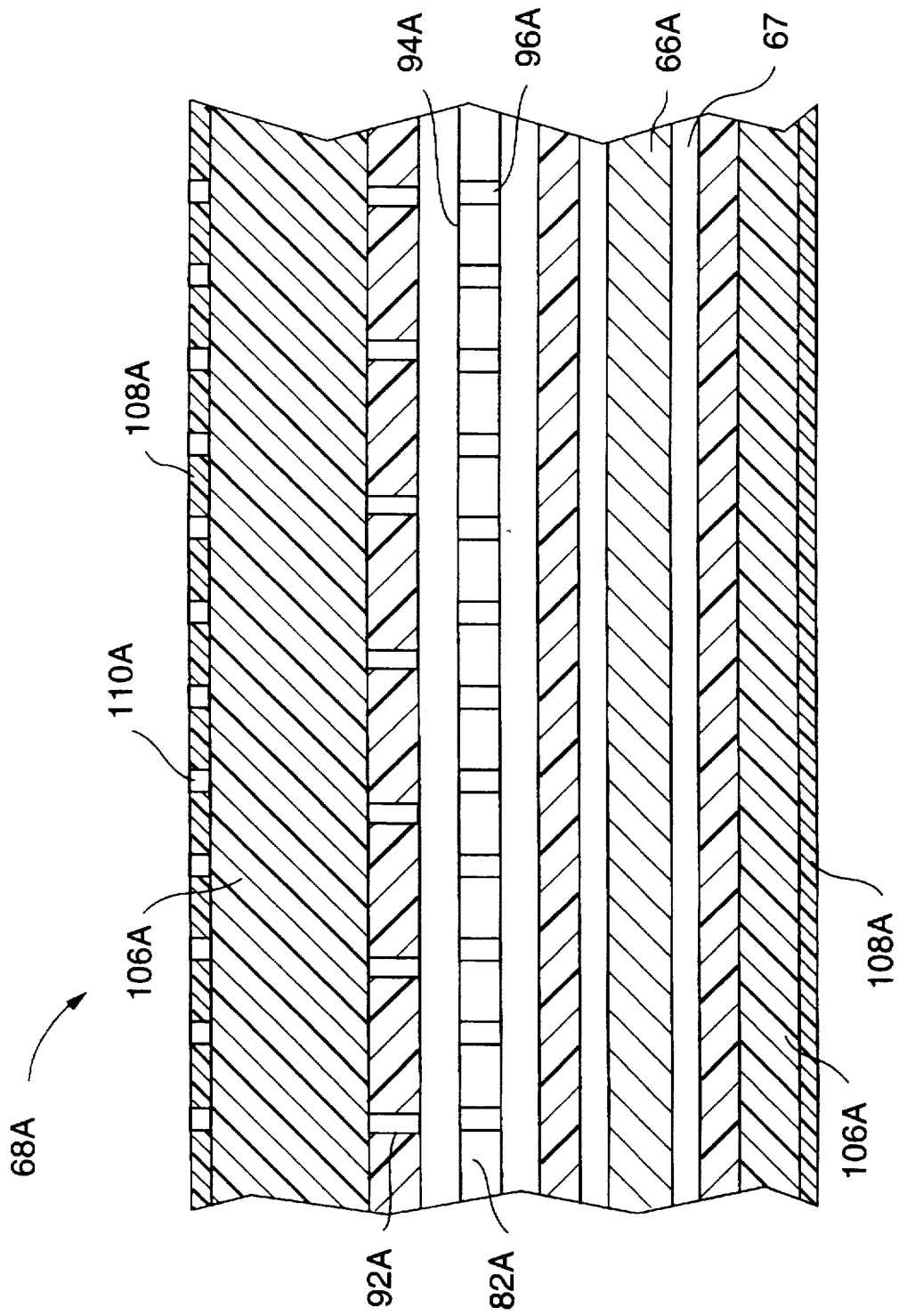
FIG. 12E is a cross-sectional view of the ablation of FIG. 12D, taken along the plane designated 12E—12E in FIG. 12D.

FIGS. 12D and 12E are cross-sectional views of the ablation section 68a and illustrate the differences between the tubing 74a and the tubing 74 of the embodiment of FIG. 7.

FIG. 12B shows the distal portion of the alternative tubing 74a. Tubing 74a is a five lumen tubing which obviates the need for the various other tubing (e.g., such as tubing 102 and 98) utilized in the embodiment shown in FIGS. 8A and 8B. Elimination of tubing makes it easier to construct the catheter to have a small diameter. Thus, it may be desirable to utilize multi-lumen of this type in the first and second embodiments or in any embodiments of the device according to the present invention.

Figure 21A:
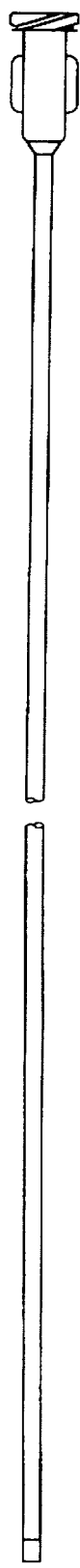
FIG. 21 are examples of various guide sheaths that may be used in conjunction with the linear lesion catheter of FIG. 18.
Figure 21B:
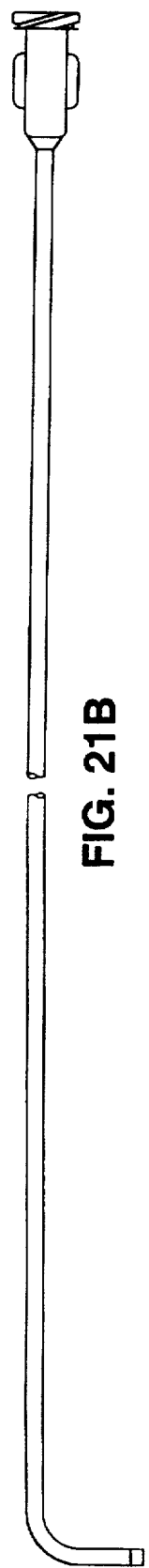
Figure 21C:
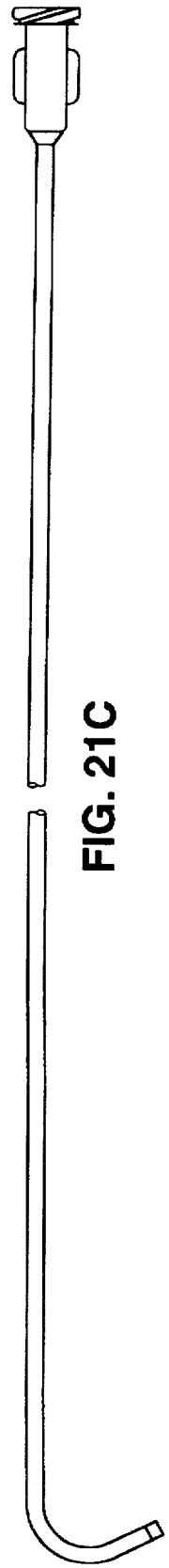
Figure 21D:
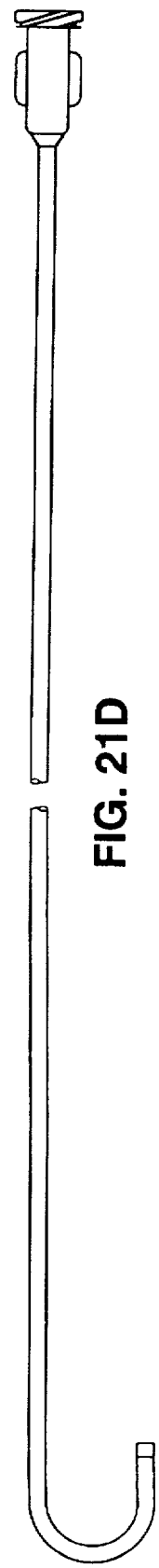

Tubing 74a includes preferably four fluid lumen 82a and a baffle lumen 67 which extend throughout its proximal (FIG. 21C) and distal (FIG. 12B) sections. Lead wires 94a extend through the fluid lumen 82a. Each of four fluid ports 88a–88d (FIG. 12A) is fluidly coupled to one of the fluid lumen 82a at the proximal end of the tubing 74a.

Baffle ribbon 66a extends through a baffle ribbon lumen 67 in the tubing 74a. Baffle ribbon lumen 67 is preferably oblong shaped to prevent rotation of the baffle ribbon 66a within it.

Referring to the proximal portion of tubing 74a shown in FIG. 12C, the proximal section tubing 74a includes the fluid lumen 82a and the baffle ribbon lumen 67 described above, and it also includes preferably two stiffening wire lumen 105. Thus, there are five lumen extending through the distal portion (FIG. 12B) of the tubing 74a and there are seven lumen extending through the proximal portion (FIG. 12C). The seven lumen proximal portion of the tubing 74a and the five lumen distal portion are fused together by conventional means.

Referring again to FIG. 12C, stiffening wires 104a extend through stiffening wire lumen 105 and thereby enhance the stiffness of the proximal portion of the catheter.

FIGS. 12D and 12E show the alternative ablation section 68a which utilizes the tubing 74a. Ablation section 68a is provided with foam segments or a foam layer, designated 106a, which is formed in an eccentric configuration such that it is thicker on one side of the ablation section 68a than it is on the other side. During use, the side of the ablation section having the thick region of foam is positioned against the target tissue which is to be ablated.

Foam 106a is enclosed within a fluid impermeable covering 108a which, as described with respect to previous embodiments, includes a plurality of tiny holes 110a. Holes 110a in the covering 108a may be formed only in the side of the covering at which the foam 106a is thickest. This helps to focus the RF energy onto the target tissue within the heart.

At the ablation section, holes 92a extend from the fluid lumen 82a through the tubing 74a to the foam layer 106a. The holes 92a are located at the side of the ablation section 68a at which the thickened foam region is located to permit the flow of conductive fluid from the fluid lumen 82a to the foam 106a and then through the holes 110a in the covering.

Rather than utilizing coil electrodes of the type described above, the alternative ablation section 68a utilizes conductive wires 94a or flat conductive ribbons, each of which is covered by an insulated coating. The wires 94a, which extend through the fluid lumen 82a, are preferably 0.005" in diameter. Exposed electrode regions 96a (FIG. 12D) that are stripped of insulative material are spaced along the portion of the wires 94a that is located within the ablation section 68a.

Operation of the embodiment of FIGS. 12A–12E is similar to the operation of the embodiment of FIG. 7 and need not be repeated here.

Figure 13A:
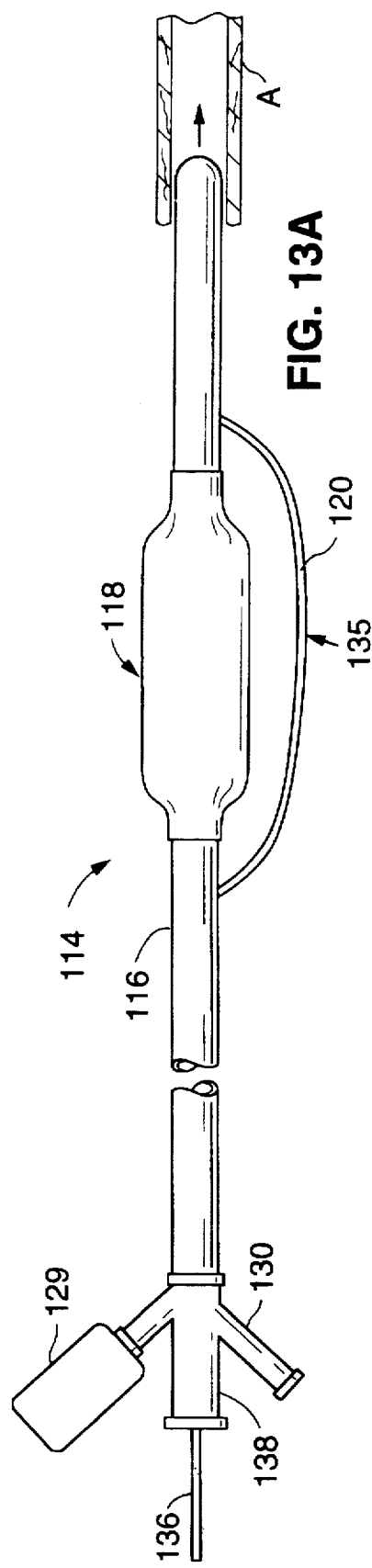
FIG. 13A is a side elevation view of a third embodiment of a linear lesion catheter according to the present invention.
Figure 13C:
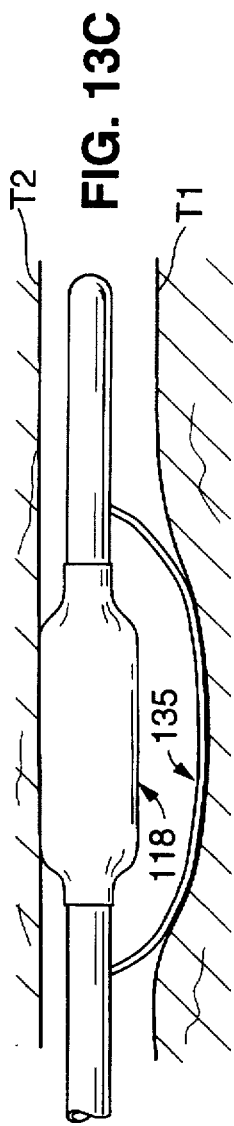
FIG. 13C is a side elevation view of a portion of the catheter of FIG. 13A illustrating the manner in which the catheter secures the ablation section against endocardial tissue.
Figure 13B:
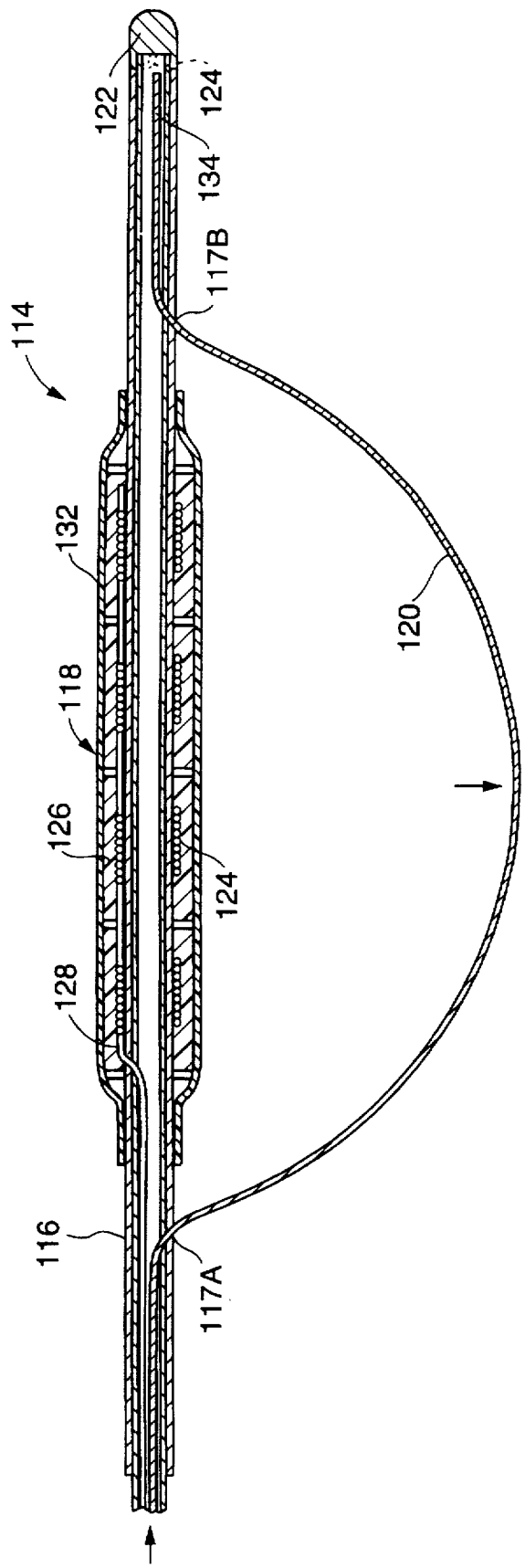
FIG. 13B is a cross-sectional side view of a distal section of the catheter of FIG. 13A.

A third embodiment of a linear lesion catheter 114 according to the present invention is shown in FIGS. 13A and 13B. Catheter 114 differs primarily from those of the first and second embodiments in that a baffle wire loop protrudes laterally, rather than longitudinally, from the main shaft.

This embodiment is generally comprised of a single lumen main shaft 116, an ablation section 118 positioned on the main shaft, and a baffle wire 120 which is slidably disposed within the main shaft 116.

Main shaft 116 is preferably constructed of a thermoplastic polymer, polyamide ether, polyurethane or other material having similar properties. A stainless steel braid (not shown) is preferably embedded in the wall of the main shaft by means conventionally known in the art to improve the torque characteristics of the main shaft. A pair of openings 117a, 117b (FIG. 13B) are formed in the side of the main shaft. Each of the openings extends from the exterior of the main shaft to the interior.

A platinum tip 122 is attached to the distal end of the main shaft 116 by an adhesive. A safety wire 124 may be soldered to the platinum tip 122 and fixed to an interior wall of the main shaft 116 to further insure that the tip 122 does not become detached from the main shaft during use. During use the tip 122 serves as a radiopaque marker which fluoroscopically indicates the position of the distal end of the catheter.

As with the previous embodiments, ablation section 118 includes a plurality of spaced coil electrodes 124, foam support segments 126, lead wires (not shown) and an infusion tube 128.

Infusion tube 128 extends from an infusion port 130 (FIG. 13A) through the main shaft 116 and then passes through an opening 129 in the main shaft 116. Along the ablation section 118, infusion tube 128 extends along the exterior surface of the main shaft 116. As with the infusion tubes 36, 82 (see FIGS. 4 and 10) of the first and second embodiments, a plurality of spaced holes (not shown) are preferably formed in the infusion tube to permit infusion of saline into and through the support segments 126.

The lead wires (not shown) extend from a female connector 129 positioned at the distal end of the catheter 114 and then pass through openings in the main shaft 116 (similar to opening 129 through which infusion tube 128 passes) at the ablation section 118.

The coil electrodes 124 are preferably coiled around the infusion tube 128, the electrode leads (not shown) and the main shaft 116 as shown in FIG. 13B. A perforated covering 132 encloses the foam support segments 126 in the manner described with respect to the first and second embodiments.

Baffle wire 120 is preferably formed of metallic stiffening wire, such as stainless steel, enclosed in thin walled shrink tube (not shown, but see FIG. 8C which shows a similar wire 66 and coating 78 configuration). Alternatively, the baffle wire 120 may be formed of a flexible braid tube. Distal end 134 (FIG. 13B) of baffle wire 120 is fixed within the distal end of the main shaft 116, near the platinum tip 122. Baffle wire 120 passes out of the main shaft 116 via opening 117b and re-enters the main shaft via opening 117a to form an arc 135 adjacent the ablation section 118. Proximal end 136 of baffle wire 120 extends freely from a connector port 138 coupled to the proximal end of the main shaft 116 (FIG. 13A).

Operation of the third embodiment of a linear lesion catheter 114 according to the present invention will next be described. To prepare the device for insertion into a patient's vessels, proximal end 136 of baffle wire 120 is pulled in a proximal direction to decrease the size of arc 135 and to thereby draw the arc 135 closer to the main shaft (see FIG. 13A). To facilitate insertion of the catheter 114 into a vessel, it may also be desirable to insert the catheter 114 into a conventional sheath catheter (not shown) so as to compress the ablation section 118 and the arc 135 close to the main shaft and to thereby prevent these structures from snagging on tissue within the vessels and the heart. Once the distal portion of the catheter 112 reaches the desired chamber of the heart, the sheath catheter is withdrawn to expose the ablation section 118 and the arc 135.

Once the ablation section 118 is within the heart chamber and positioned adjacent a region of the endocardium which is to be ablated, proximal end 136 of baffle wire 120 is advanced in a distal direction, as indicated by the arrow in FIG. 13B. Because distal end 134 of the baffle wire 120 is fixed within the main shaft, distal sliding of the baffle wire 120 causes an additional length of the baffle wire 120 to pass out of the main shaft via the hole 117a and thus increases the size of the arc. As the size of the arc increases, the arc pushes against adjacent tissue T1 and thus leverages the ablation section 118 against the portion T2 of the endocardium on which a lesion is to be formed. (See FIG. 13C). Pressing the ablation section 118 against the endocardium in this manner helps the ablation section 118 to conform to the surface of the tissue T2 and thus helps to ensure that sufficient contact is made between the ablation section 118 and the endocardium.

Next, delivery of saline and RF energy to the ablation section 118 is carried out as described with respect to the first and second embodiments to cause the lesion to be formed.

Figure 14B:
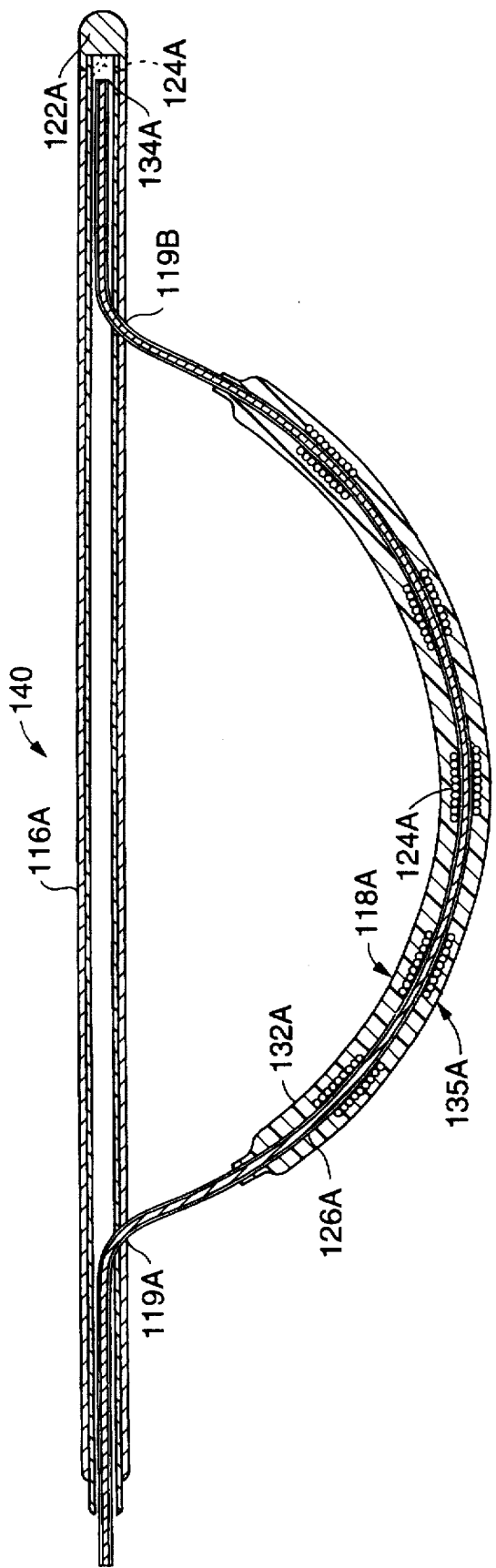
FIG. 14B is a cross-sectional side view of a distal section of the catheter of FIG. 14A.

A fourth embodiment of a catheter 140 according to the present invention is shown in FIG. 14. The fourth embodiment is similar to the third in that a baffle wire loop protrudes from the main shaft. It differs from the fourth embodiment in that in includes an ablation section on the baffle wire.

As with the catheter 114 of the third embodiment (FIG. 13A), catheter 140 includes a main shaft 116a, and an ablation section 118a. Main shaft includes a platinum tip 122a similar to the platinum tip 122 of FIG. 13B, and it further includes a pair of holes 119a, 119b. At the proximal end of the main shaft 116 is a connector having an infusion port 130a, a second port 138a, and a female connector 129a.

A baffle wire 120a extends through the main shaft 116a and includes a distal end 134a fixed to the distal end of the main shaft 116a. A free proximal end 136a extends from connector port 138a in the main shaft. A section of the baffle wire 120a extends through holes 119a, 119b in the main shaft 116a to form an arc 135a.

As with the above-described embodiments, ablation section 118a preferably includes a perforated covering 132a, foam support segments 126a, coil electrodes 124a, lead wires (not shown) and an infusion tube (not shown). These elements are arranged on the arc 135a formed by baffle wire 120a in a manner which is preferably similar to the manner in which the covering 44, foam 42, electrodes 40, leads 39, baffle wire 20, and infusion tube 36 are arranged in the first embodiment. Reference is therefore made to FIGS. 4 and 5 and the description thereof.

Operation of the fourth embodiment of a linear lesion catheter 140 according to the present invention will next be described. To prepare the device for insertion into a patient's vessels, free end 136a of baffle wire 120a is pulled in a proximal direction to draw the arc 135a closer to the main shaft (see FIG. 14A). The catheter 140 may be inserted into a conventional sheath catheter (not shown) so as to compress the ablation section 118a and the arc 135a close to the main shaft 116a to prevent these structures from snagging on tissue within the vessels and the heart. The sheath catheter is withdrawn to expose the ablation section 118 after the distal portion of the catheter 112a has been fed through the patient's vessels and positioned in the desired chamber of the heart.

Once the ablation section 118a is within the heart chamber, free end 136a of baffle wire 120a is advanced in a distal direction, causing a portion of the baffle wire 120a to pass out of the main shaft via the hole 119a thereby increasing the size of the arc 135a. As the size of the arc increases, the arc and the main shaft push against opposing tissue surfaces T1, T2 and thus leverage the ablation section 118a against the portion T2 of the endocardium on which a lesion is to be formed. (See FIG. 14C). Pressing the ablation section 118a against the endocardium in this manner helps the ablation section 118a to conform to the surface of the endocardium and thus helps to ensure that sufficient contact is made between the ablation section 118 and the endocardium to create a continuous transmural lesion.

Once the ablation section is properly positioned and baffled against the appropriate section of the endocardium, saline and RF energy are delivered to the ablation section 118 as described with respect to the first and second embodiments. The procedure is repeated to create multiple lesions on the endocardium.

Figure 15A:
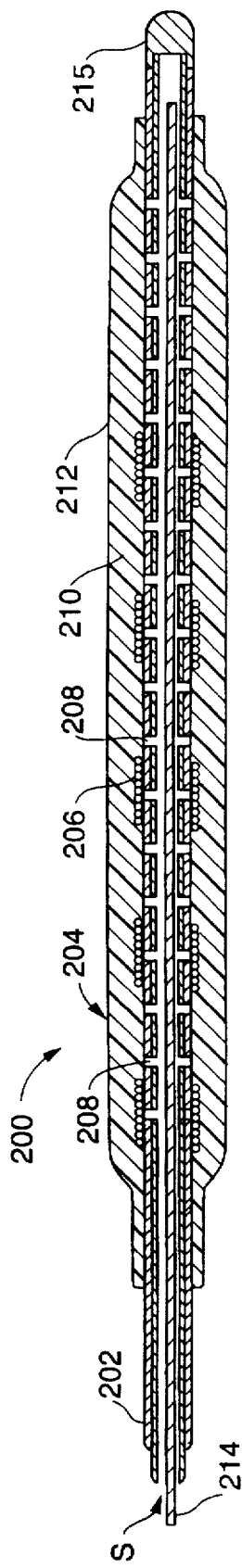
FIG. 15A is a cross-sectional side view of a fifth embodiment of a linear lesion catheter according to the present invention.

It should be understood that the various features of the preferred embodiments need not be used in combination with one other. For example, referring to FIG. 15A, a catheter 200 (a fifth embodiment) according to the present invention may be provided without a baffle wire as found in the previously described embodiments. Catheter 200 includes a main shaft 202 (preferably having a diameter of 7 French) and an ablation section 204 formed over the main shaft 202.

At the ablation section 204, a plurality of electrodes 206 are coiled around the main shaft 202, and (also at the ablation section 204) a plurality of spaced holes 208 are formed in the main shaft. A foam support structure 210 (which may be segmented as in prior embodiments) is formed around the main shaft and electrodes 206, and the support structure 210 is enclosed by a perforated covering 212. A core wire 214 extends through the central lumen of the main shaft 202. Wire 214 may alternatively be a pull wire of a type which may be used to steer the catheter 200 through a patient's vessels and heart.

Figure 15B:
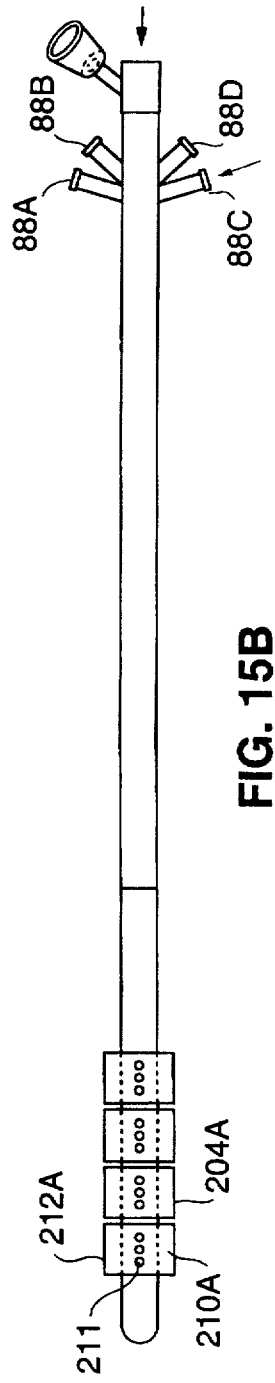
FIG. 15B is a side plan view of a embodiment similar to the embodiment of FIG. 15A, in which each of the foam segments is provided with a separate covering.

As shown in FIG. 15B, foam segments 210a may each be provided with separate coverings 212a, each of which is provided with a plurality of holes 211 along one side. It is desirable to provide four such 20 mm wide segments 210a, each spaced from the other segments 210a by approximately 1 mm. Preferable, multiple lumen tubing having the configuration shown in FIGS. 12B and 12C is utilized, with each of the fluid lumen (see lumen 82a in FIGS. 12B and 12C) directing fluid from one of the fluid portions 88a–88d to one of the foam segments 210a.

During use the catheter 200 is inserted via vessels into a chamber of the heart, and positioned against the endocardial surface. Saline S is introduced into the central lumen of main shaft 202 (which in this embodiment serves as the infusion tube) and passes through the holes 208 into the foam structure 210. RF energy is delivered to the electrodes 206 via lead wires (not shown) as described with respect to previous embodiments.

The outward pressure of the saline S within covering 212 causes the covering 212 to balloon out slightly and thereby improves contact between the ablation section 204 and the endocardium. Saline passes from the foam out of the ablation section via the perforations (not shown) in the covering 212 and in doing so creates an improved path of conductivity between the electrodes 206 and the endocardium.

As mentioned above, the foam support structure of the FIG. 15A embodiment and the previous embodiments may be replaced by other support structures which can press the covering of the ablation section against the endocardial wall during use. For example, small inflatable balloons 215 (FIG. 16, a sixth embodiment) may be positioned inside the covering 212 and provided with inflation tubes 216 which provide flow paths for the introduction of an inflation medium (such as air or fluid) into the balloons 215 during use. Alternatively, the foam and covering may be eliminated from the apparatus as shown in FIG. 17 (seventh embodiment), in which case the conductive fluid or saline flows through openings 208 in the main shaft and is utilized primarily to cool the ablation electrodes 206, although it may also create a conductive path between the electrodes and target tissue. The electrodes 206 may be formed into coils, braids, or other configurations.

An eighth embodiment (FIGS. 18–23C) of the present invention is generally similar to the first embodiment except that the catheter contains additional features allowing the ablation section to be more easily maneuvered. The additional features include the use of a guide sheath and one or more pullwires. Except for these features, the other elements of this catheter may be as previously described for the other embodiments of the present invention.

Figure 18:
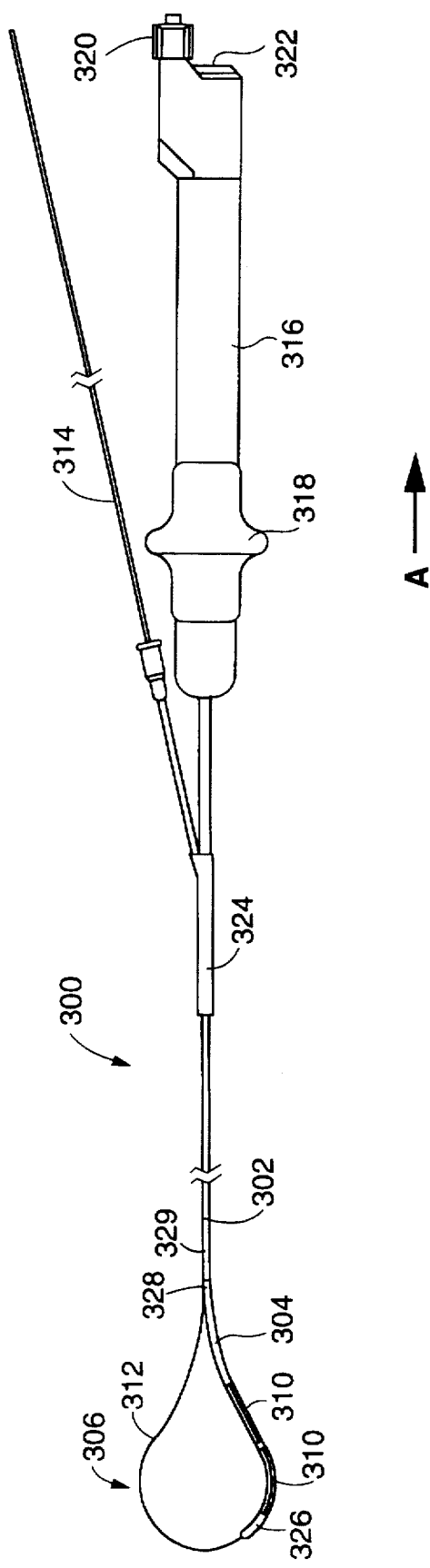
FIG. 18 is a side view of an eighth embodiment of a linear lesion catheter according to the present invention in which the guide sheath is not shown so as to simplify the drawing.
Figures 19A, 19B:
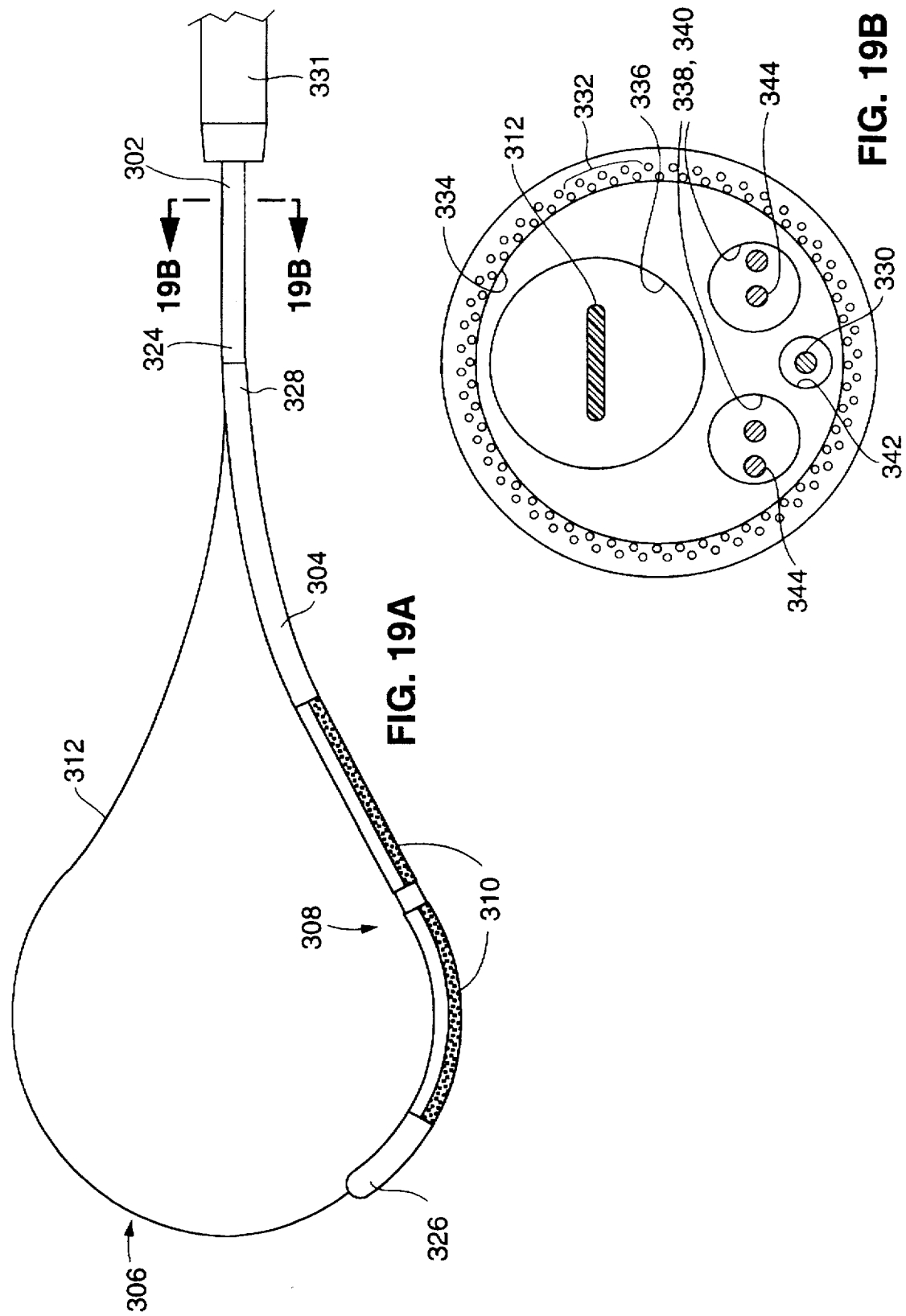
FIG. 19A is an enlarged view of the loop section of the eighth embodiment.
FIG. 19B is a cross-sectional view of the main shaft of the linear lesion catheter of FIG. 18, taken along the plane designated 19B—19B in FIG. 19A.

As illustrated by FIG. 18, catheter 300 generally includes a main shaft 302, a deflectable shaft 304, a baffle ribbon 312, an ablation section 308 formed on the distal portion 326 of deflectable shaft 304, and a guide sheath 331 (see FIG. 19A). Proximal end 328 of deflectable shaft 304 and distal end 329 of main shaft 302 are contiguous so as to form one continuous shaft. Although guide sheath 331 is initially slidably disposed around main shaft 302, deflectable shaft 304, and baffle ribbon 312, the guide sheath is subsequently retracted or the catheter 300 is advanced to expose loop 306.

In preferred embodiments, the ablation section 308 has a length of approximately between 2 and 10 cm and an outer diameter of approximately between 3 and 5 cm. Because this embodiment of the present invention uses a guide sheath, main shaft 302 and deflectable shaft 304 preferably have diameters that are smaller, approximately between 1.5 mm and 3 mm, than the main shafts of previously described embodiments. The diameter of guide sheath 331 is such that main shaft 302 and loop 306 which includes ablation section 308 and deflectable shaft 304, may be slidably received therein and is preferably approximately between 3 and 4 mm. However, the lengths and diameters of ablation section 308, deflectable shaft 304, main shaft 302, and guide sheath 331 may be outside of these ranges.

Referring to FIG. 19A, both main shaft 302 and deflectable shaft 304 may be made from the same material. Suitable materials include thermoplastic polymer, polyamide ether, polyurethane and other materials having similar properties that are known in the art.

Deflectable shaft 304 differs from main shaft 302 in that it is more flexible (i.e., less rigid or stiff). This difference in flexibility allows deflectable shaft 304 to deflect to any angle, preferably up to 120°, from its non-deflected state without substantially affecting main shaft 302. In preferred embodiments, the rigidity of main shaft 302 is approximately between 65 and 80 durometers and the rigidity of deflectable shaft 304 is approximately between 30 and 40 durometers.

One end of pullwire 330 is attached to proximal portion (at or near end 328) of deflectable shaft 304 by conventional means and the other end is attached to deflection knob 318 in handle 316. Pullwire 330 can be actuated when deflection knob 318 is slidably retracted along handle 316 in the direction shown by arrow A in FIG. 18. The retraction of knob 318 causes deflectable shaft 304 to be deflected. When the knob is moved back along the handle in a direction opposite to arrow A, shaft will return to its nondeflected state. Alternate pullwire actuation means may also be used. Although this embodiment utilizes only one pullwire, additional deflection points may be created by using a plurality of pullwires.

Referring to FIG. 19B, a stainless steel braid 332 is preferably embedded in the wall of the main shaft 302 by means conventionally known in the art. The inclusion of the braid improves the torque characteristics of the main shaft and thus makes the main shaft easier to maneuver through a patient's vessels and heart. A Teflon® lining 334, also conventional in the art, preferably lines the interior wall of the main shaft to cover wire braid 332. To minimize the possibility for tissue trauma as the ablation catheter is fed through a patient's blood vessels and heart during use, the braid is preferably absent from deflectable shaft 304. This leaves the catheter tip sufficiently flexible to yield when advanced against obstacles within the vessels and heart.

Still referring to FIG. 19B, baffle ribbon 312 extends through a lumen 336 in deflectable shaft 304 and main shaft 302 and is preferably covered with Teflon® coating. As shown, baffle ribbon 312 preferably has a substantially flat cross-section (i.e., rectangular or oblong to prevent the baffle ribbon from rotating about its longitudinal axis during use.

One end of baffle ribbon 312 is fixed to main shaft 302, preferably at the junction between the deflectable shaft 304 and the main shaft 302 by conventional methods known in the art. From this fixed point, baffle ribbon 312 exits out of a lumen in the distal portion 329 of main shaft 302 and re-enters at the most distal end 326 of deflectable shaft 304, thus forming loop 306. Alternatively, from the fixed point, baffle ribbon 312 may extend through deflectable shaft 304 and re-enter a lumen in the distal portion 329 of main shaft 302, thus forming loop 306. However, it should be appreciated that the fixed position of the baffle ribbon 312 and the exit or re-entry lumen can be selected at a variety of positions along the main shaft 302 so as to form various loop geometries.

Once baffle ribbon 312 enters main shaft 302 after forming loop 306, it spans through substantially the entire length of main shaft 302 and diverges from main shaft 302 immediately prior to the main shaft being coupled to handle 316. The portion of baffle ribbon which diverges from main shaft 302 may be advanced or retracted to control the size of loop 306. In preferred embodiments, means for stiffening the portion of baffle ribbon which diverges from main shaft 302 is used, like attaching baffle ribbon 312 to a more rigid wire 314. The increased rigidity of wire 314 allows baffle wire 312 to be advanced and retracted more easily. FIGS. 20A and 20B illustrates the portion of catheter 300 where wire 314 which has been attached to baffle ribbon 312 diverges from main shaft 302.

In the present embodiment, two infusion tubes extend through ablation section 308 and through deflectable shaft 304 and main shaft 302. The catheter illustrated by FIGS. 18–23C includes four lumens, 336, 338, 340, and 342. Lumen 336 contains baffle ribbon 312 and lumen 342 contains pullwire 330. Lumens 338 and 340 each respectively contain an infusion tube (not pictured) and a plurality of lead wires 344. Each infusion tube includes a sealed distal end which terminates near its respective electrodes 310 and a proximal end fluidly coupled with a fluid port formed in handle 316. FIG. 18 illustrates one of the two fluid ports, 320.

As described with respect to previous embodiments, a plurality of spaced holes, 346, extend through the portion of the infusion tubes positioned at ablation section 308 of catheter 300 (see FIG. 19C). In addition, a plurality of lead wires 344 (FIG. 19B) which are preferably formed of copper, extend through ablation section 308 and further extend through deflectable shaft 304 and main shaft 302 terminating in a female adapter 322 (FIG. 18) formed into handle 316.

Referring to FIGS. 19C–F, the two electrodes, 310, consist of a plurality of metallic contacts, 348, mounted onto deflectable shaft 304. Deformable members, or foam support segments 350 surround electrodes 310. Suitable material for forming foam support segments 350 include open cell polyurethane, cotton-like material, open-cell sponge, hydrogels, or other compressible materials which are permeable by conductive fluids such as saline. As previously described, the foam support segments are enclosed within a covering formed of heat shrink polyethylene silicone, or other polymeric materials having a plurality of small holes 346 or perforations formed in it.

As described previously, loop 306, deflectable shaft 304, and main shaft 302 are slidably received within guide sheath 331. The guide sheath may be made of the same material as main shaft 302. Suitable materials include thermoplastic polymer, polyamide ether, polyurethane and other materials having similar properties that are known in the art. As illustrated by FIG. 21, guide sheath 331 may be substantially straight (360) or may form a curve at its tip so as to allow ablation section 308 to be positioned at an angle with respect to the guide sheath. Suitable curve angles include but are not limited to 90° (362), 120° (364), and 180° (366).

With use of guide sheath 331 and pullwire 330, ablation section 308 may be manipulated in three different ways (see FIG. 22). First, as before, the size of loop 306 may be increased or decreased by causing baffle ribbon 312 to be advanced or retracted. Second, deflectable shaft 304 which contains ablation section 308 may be deflected by pullwire 330. Finally, loop 306 may be rotated with respect to guide sheath 331 since both deflectable shaft 304 and main shaft 302 are slidably received into guide sheath 331 and not affixed therein.

Figure 23B:
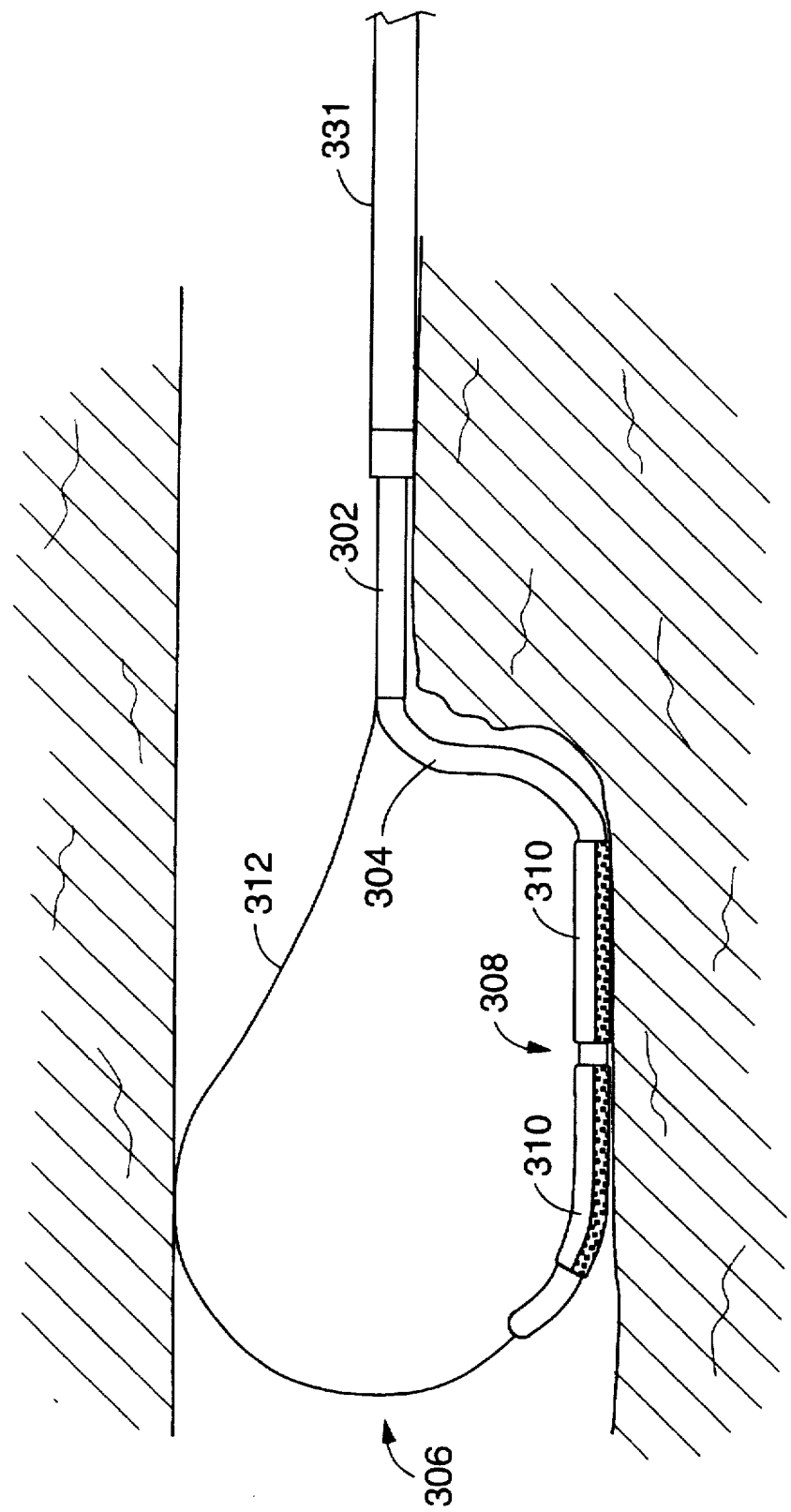
Figure 23C:
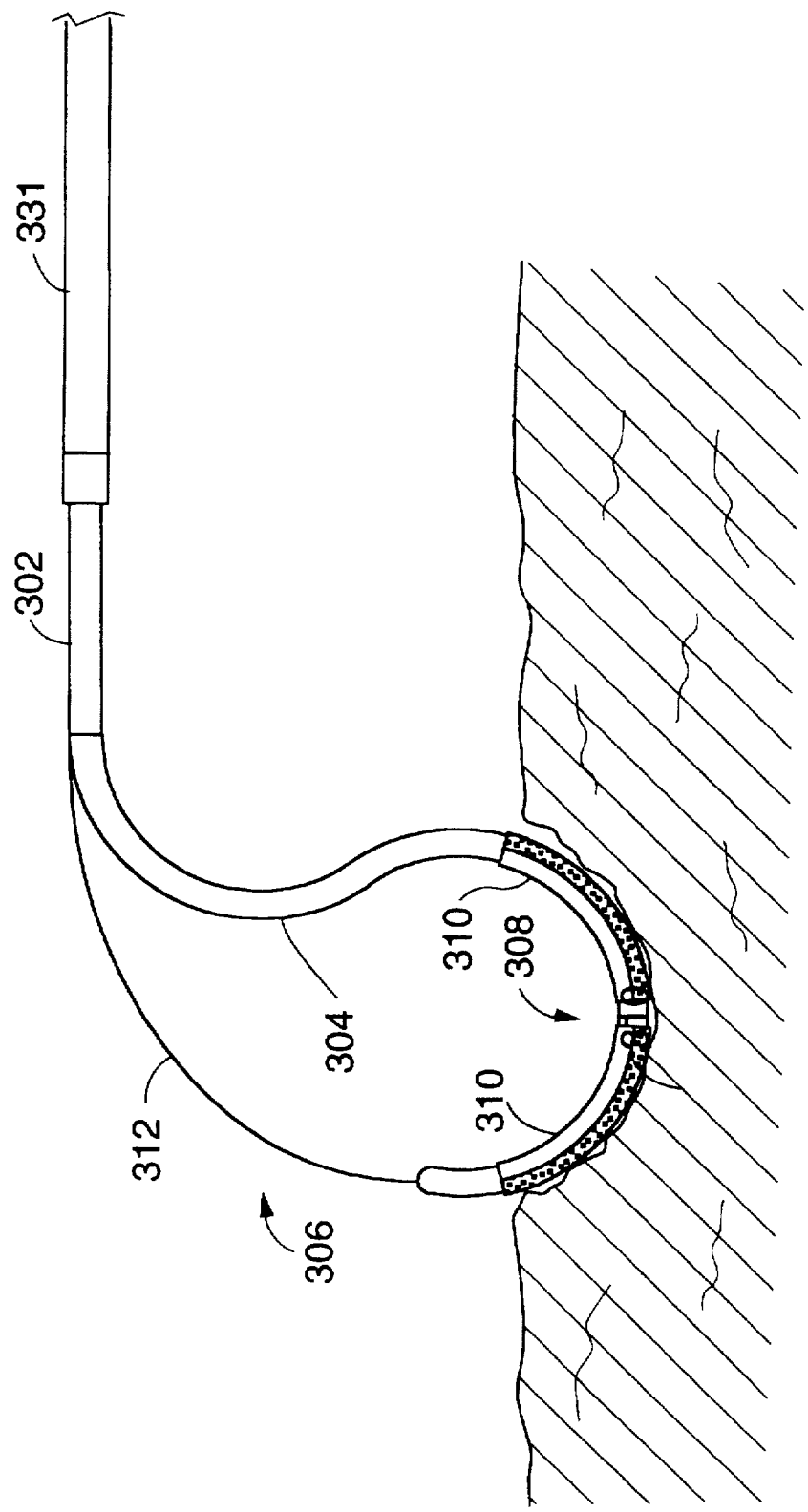

Operation of the eighth embodiment of the present invention will be next described. Prior to beginning the procedure, loop 306 and main shaft 302 are withdrawn into guide sheath 331. Once the distal end of guide sheath is positioned within the appropriate chamber of the heart, as illustrated by FIG. 23A, loop 306 which includes ablation section 308 and deflectable shaft 304 is pushed out of guide sheath 331. The height, location and size of loop 306 may be adjusted to position ablation section 308 against the desired surface within the heart chamber and to maintain contact between the ablation surface of the catheter and the target surface within the heart chamber. Because deflectable shaft 304 and main shaft 302 are not affixed to guide sheath 331, loop 306 may be rotated with respect to the guide sheath. Moreover, as illustrated by FIGS. 23B and 23C, pullwire 330 may be actuated to cause deflectable shaft 304 to be deflected a predetermined angle with respect to its non-deflected state. Once ablation section 308 is properly positioned with respect to the target tissue, delivery of saline and RF energy to ablation section 308 is carried out as described with respect to the first and second embodiments to cause the lesions to be formed.

Preferred embodiments and several alternative embodiments of a linear lesion catheter have been described herein. It should be appreciated that these embodiments have been given by way as example and are not intended to limit the scope of the appended claims.

What is claimed is:

1. An apparatus for ablating body tissue, comprising:
   an elongate tubular member having an opening;
   a baffle member having a distal portion slidably disposed within the tubular member, the baffle member slidable between a first position in which the distal portion extends from the opening and is folded over itself, and a second position in which the distal portion of the baffle member is contained within the elongate tubular member;
   an ablation section carried by the baffle member;
   at least one electrode carried by the ablation section;
   a fluid permeable deformable member at least partially covering the electrodes;
   means for delivering current to the electrode; and,
   means for delivering conductive fluid through the deformable member to the ablation section to cause said fluid to create a conductive path between the electrodes and the tissue when the electrodes are positioned adjacent to body tissue.

2. The apparatus of claim 1 wherein the baffle member includes a fixed distal end attached to the tubular member and a free proximal end, the free proximal end slidable relative to the tubular member to move the baffle member between the first and second positions.

3. The apparatus of claim 2 wherein the free proximal end of the baffle member diverges from the tubular member.

4. The apparatus of claim 3 wherein the baffle member has a substantially flat cross-section.

5. The apparatus of claim 3 wherein
   the apparatus further comprises a second tube, wherein a portion of the baffle member is slidably received within the second tube;
   the ablation element is carried by the second tube; and
   when the baffle member is in the first position, the second tube is slidable over the loop to reposition the ablation element with respect to the loop.

6. An apparatus for creating lesions in body tissue, comprising:
   an elongate tubular member having a distal portion, a first opening, and a second opening, the first opening being more distal relative to the second opening;
   a baffle member having a fixed end attached to the tubular member and a free proximal end slidable relative to the tubular member, the baffle member forming a loop by extending from the fixed end, out the first opening of the tubular member and re-entering the tubular member at the second opening;
   a pullwire having a fixed end attached to the distal portion of the tubular member;
   means for actuating the pullwire to bend the distal portion of the tubular member;
   an ablation section carried by the distal portion of the tubular member;
   at least one electrode carried by the ablation section;
   a fluid permeable deformable member at least partially covering the electrodes;
   means for delivering current to the electrode; and,
   means for delivering conductive fluid through the deformable member to the ablation section to cause said fluid to create a conductive path between the electrodes and the tissue when the electrodes are position adjacent to body tissue.

7. An apparatus for creating lesions in body tissue, comprising:
   an elongate tubular member having a distal portion, a first opening, and a second opening, the first opening being more distal relative to the second opening;
   a baffle member having a fixed end attached to the tubular member and a free proximal end slidable relative to the tubular member, the baffle member forming a loop by extending from the fixed end, out the second opening of the tubular member and re-entering the tubular member at the first opening;
   a pullwire having a fixed end attached to the distal portion of the tubular member;
   means for actuating the pullwire to bend the distal portion of the tubular member;
   an ablation section carried by the distal portion of the tubular member;
   at least one electrode carried by the ablation section;
   a fluid permeable deformable member at least partially covering the electrodes;
   means for delivering current to the electrode; and,
   means for delivering conductive fluid through the deformable member to the ablation section to cause said fluid to create a conductive path between the electrodes and the tissue when the electrodes are position adjacent to body tissue.

8. The apparatus of claim 7 further comprising a guide sheath wherein the elongate member and the baffle member is slidably disposed therein.

9. The apparatus of claim 7 wherein the free proximal end of the baffle member diverges from the tubular member.

10. The apparatus of claim 7 wherein the baffle member has a substantially flat cross-section.

11. The apparatus of claim 7 wherein the distal portion of the tubular member is composed of a more flexible material.

12. The apparatus of claim 7 wherein the apparatus further includes a covering on the deformable member, the covering formed of a material substantially impermeable to fluid, the covering including at least one opening sized to allow passage of fluid out of the covering.

13. The apparatus of claim 12 wherein the deformable member includes a layer of foam over the electrodes.

14. The apparatus of claim 7 further comprising a plurality of pullwires and a plurality of means for actuating said pullwires.

15. A method of forming a linear lesion comprising using an apparatus of any one of claims 6–14.

16. The method of claim 15 further comprising positioning the loop near a tissue to be ablated.

17. The method of claim 16 wherein the positioning step includes adjusting the size of the loop by advancing or retracting the free proximal end of the baffle member.

18. The method of claim 16 wherein the positioning step includes adjusting the position of the loop by deflecting the distal portion of the tubular member.

19. A method of forming a linear lesion comprising using an apparatus of claim 8 and positioning the loop near a tissue to be ablated, and adjusting the position of the loop by rotating the loop with respect to the guide sheath.

20. An apparatus for ablating body tissue, comprising:
   an elongate tubular member having a bendable distal section;
   a baffle loop carried at the distal end of the tubular member;
   a pullwire extending through the tubular member, the pullwire having a fixed distal end and a proximal end moveable to adjust the bend of the distal section of the tubular member; and an ablation element carried by the bendable distal section of the tubular member.

21. An apparatus for ablating body tissue, comprising:

an elongate tubular member having an opening and a distal end;

an elongate shaft member slidably disposed within the elongate tubular member;

a baffle member carried by the shaft member and having a distal portion slidably disposed within the tubular member, the baffle member slidable between a first position in which the distal portion extends from the opening and is folded over itself, and a second position in which the distal portion of the baffle member is contained within the elongate tubular member; and an ablation element carried by the distal end of the shaft member.

22. The apparatus of claim 21 wherein the distal end of the shaft member is bendable and wherein the apparatus further comprises:

a pullwire extending through the elongate shaft member, the pullwire having a fixed distal end and a proximal end moveable to adjust the bend of the distal section of the shaft member.

23. The apparatus of claim 21 wherein the baffle member includes a free proximal end extending laterally of the shaft member.

* * * * *